United States Patent
Pedersen et al.

(10) Patent No.: US 12,296,148 B2
(45) Date of Patent: *May 13, 2025

(54) AUTO INJECTOR WITH TEMPERATURE CONTROL

(71) Applicant: Ascendis Pharma A/S, Hellerup (DK)

(72) Inventors: Per Mølgaard Pedersen, Struer (DK); Steen Jensen, Dragør (DK); Henrik Egesborg, Hellerup (DK); Bjørn Knud Andersen, Struer (DK)

(73) Assignee: Ascendis Pharma A/S, Hellerup (DK)

( * ) Notice: Subject to any disclaimer, the term of this patent is extended or adjusted under 35 U.S.C. 154(b) by 280 days.

This patent is subject to a terminal disclaimer.

(21) Appl. No.: 17/741,314

(22) Filed: May 10, 2022

(65) Prior Publication Data

US 2022/0265931 A1    Aug. 25, 2022

Related U.S. Application Data

(63) Continuation of application No. 16/060,600, filed as application No. PCT/EP2016/082857 on Dec. 29, 2016, now Pat. No. 11,351,305.

(30) Foreign Application Priority Data

Dec. 30, 2015   (EP) .................................... 15203168
Sep. 23, 2016   (EP) .................................... 16190461

(51) Int. Cl.
*A61M 5/20*    (2006.01)
*A61M 5/24*    (2006.01)
(Continued)

(52) U.S. Cl.
CPC ............ *A61M 5/2066* (2013.01); *A61M 5/20* (2013.01); *A61M 5/24* (2013.01);
(Continued)

(58) Field of Classification Search
CPC .. A61M 5/2066; A61M 5/24; A61M 5/31573; A61M 5/31576; A61M 5/326;
(Continued)

(56) References Cited

U.S. PATENT DOCUMENTS 4,024,864 A    5/1977  Davies
4,677,980 A    7/1987  Reilly et al.
(Continued)

FOREIGN PATENT DOCUMENTS

CN    101905048    12/2010
CN    102413855    4/2012
(Continued)

OTHER PUBLICATIONS

US 11,957,880 B2, 04/2024, Jensen et al. (withdrawn)
(Continued)

*Primary Examiner* — Lauren P Farrar
(74) *Attorney, Agent, or Firm* — Knobbe, Martens, Olson & Bear, LLP

(57) ABSTRACT

Disclosed is an auto injector and a method for administering a medicament. The auto injector comprising: a housing; a cartridge receiver; a drive module coupled to move a plunger rod configured to move a first stopper; a temperature sensor configured to provide a temperature signal indicative of the temperature of the medicament in the cartridge; a processing unit configured to: receive the temperature signal; control the drive module to move the plunger rod from a first plunger rod position to a mix plunger rod position wherein the movement from the first plunger rod position to the mix plunger rod position is based on the temperature signal.

33 Claims, 13 Drawing Sheets

(51) Int. Cl.
*A61M 5/315* (2006.01)
*A61M 5/32* (2006.01)

(52) U.S. Cl.
CPC .... *A61M 5/31511* (2013.01); *A61M 5/31573* (2013.01); *A61M 5/31576* (2013.01); *A61M 5/326* (2013.01); *A61M 2005/2411* (2013.01); *A61M 2005/31588* (2013.01); *A61M 2005/3267* (2013.01); *A61M 2205/332* (2013.01); *A61M 2205/3368* (2013.01); *A61M 2205/50* (2013.01); *A61M 2205/502* (2013.01); *A61M 2205/6063* (2013.01); *A61M 2205/82* (2013.01); *A61M 2205/8206* (2013.01)

(58) Field of Classification Search
CPC ............... A61M 5/31511; A61M 5/20; A61M 2205/50; A61M 2205/82; A61M 2005/2411; A61M 2005/31588; A61M 2005/3267; A61M 2205/332; A61M 2205/3368; A61M 2205/502; A61M 2205/6063; A61M 2205/8206
See application file for complete search history.

(56) References Cited

U.S. PATENT DOCUMENTS

| | | | |
|---|---|---|---|
| 5,739,508 | A | 4/1998 | Uber, III |
| 5,808,203 | A | 9/1998 | Nolan, Jr. et al. |
| 6,368,314 | B1 | 4/2002 | Kipfer et al. |
| 9,173,995 | B1 | 11/2015 | Tucker |
| 10,384,031 | B1 | 8/2019 | Acker et al. |
| 10,835,677 | B2 | 11/2020 | Fabricius et al. |
| 11,179,524 | B2 | 11/2021 | Pedersen et al. |
| 11,351,305 | B2 | 6/2022 | Pedersen et al. |
| 11,406,760 | B2 | 8/2022 | Olesen et al. |
| 11,517,673 | B2 | 12/2022 | Pedersen et al. |
| 11,524,115 | B2 | 12/2022 | Jacobsen et al. |
| 11,607,496 | B2 | 3/2023 | Fabricius et al. |
| 11,684,724 | B2 | 6/2023 | Egesborg et al. |
| 11,738,147 | B2 | 8/2023 | Olesen et al. |
| 11,969,581 | B2 | 4/2024 | Pedersen et al. |
| 12,005,241 | B2 | 6/2024 | Pedersen et al. |
| 2002/0016573 | A1 | 2/2002 | Munk |
| 2002/0107477 | A1 | 8/2002 | Kipfer |
| 2003/0083626 | A1 | 5/2003 | Munk et al. |
| 2003/0205587 | A1 | 11/2003 | Tribe |
| 2005/0261634 | A1 | 11/2005 | Karlsson |
| 2006/0178630 | A1 | 8/2006 | Bostrom et al. |
| 2009/0036846 | A1 | 2/2009 | Dacquay et al. |
| 2009/0209883 | A1 | 8/2009 | Higgins et al. |
| 2009/0299328 | A1 | 12/2009 | Mudd et al. |
| 2010/0069842 | A1* | 3/2010 | Dos Santos ............ A61M 5/20 604/113 |
| 2010/0094309 | A1 | 4/2010 | Boukhny et al. |
| 2010/0211005 | A1* | 8/2010 | Edwards ............ A61M 15/008 604/82 |
| 2011/0313395 | A1 | 12/2011 | Krulevitch et al. |
| 2012/0078185 | A1 | 3/2012 | Smith et al. |
| 2012/0204997 | A1 | 8/2012 | Winn et al. |
| 2012/0283655 | A1 | 11/2012 | Plumptre et al. |
| 2013/0079708 | A1 | 3/2013 | Wiimpenny et al. |
| 2013/0193073 | A1* | 8/2013 | Hogard ............ A61M 1/15625 210/637 |
| 2013/0211326 | A1 | 8/2013 | Dasbach et al. |
| 2013/0211327 | A1 | 8/2013 | Osman et al. |
| 2013/0226134 | A1* | 8/2013 | Schabbach .......... A61M 5/3129 604/67 |
| 2013/0245545 | A1 | 9/2013 | Arnold et al. |
| 2013/0281965 | A1* | 10/2013 | Kamen .................. G16H 20/17 604/67 |
| 2013/0296807 | A1 | 11/2013 | Lintern et al. |
| 2014/0012229 | A1 | 1/2014 | Bokelman et al. |
| 2014/0114277 | A1 | 4/2014 | Eggert et al. |
| 2014/0142514 | A1 | 5/2014 | Elahi et al. |
| 2014/0166915 | A1 | 6/2014 | Ishibashi et al. |
| 2014/0188076 | A1 | 7/2014 | Kamen et al. |
| 2014/0193788 | A1 | 7/2014 | Groves et al. |
| 2014/0207106 | A1 | 7/2014 | Bechmann et al. |
| 2014/0221925 | A1 | 8/2014 | Kondoh et al. |
| 2014/0358093 | A1 | 12/2014 | Soerensen et al. |
| 2015/0045729 | A1 | 2/2015 | Denzer et al. |
| 2015/0051538 | A1* | 2/2015 | Hata .................. A61M 5/1452 604/154 |
| 2015/0088089 | A1 | 3/2015 | Bartlett, II et al. |
| 2015/0122338 | A1 | 5/2015 | Hunter et al. |
| 2015/0231334 | A1* | 8/2015 | Buchine .................. A61P 9/02 514/415 |
| 2015/0306316 | A1 | 10/2015 | Bruggemann |
| 2015/0320932 | A1 | 11/2015 | Draper et al. |
| 2015/0359967 | A1 | 12/2015 | Steel et al. |
| 2015/0367074 | A1 | 12/2015 | Draper et al. |
| 2015/0367075 | A1 | 12/2015 | Cave |
| 2015/0374930 | A1 | 12/2015 | Hyde et al. |
| 2017/0119969 | A1 | 5/2017 | McCullough et al. |
| 2017/0196702 | A1 | 7/2017 | Agarwal |
| 2018/0094309 | A1 | 4/2018 | Boukhany |
| 2018/0236181 | A1 | 8/2018 | Marlin et al. |
| 2018/0369481 | A1 | 12/2018 | Pedersen et al. |
| 2018/0369482 | A1 | 12/2018 | Pedersen et al. |
| 2018/0369483 | A1 | 12/2018 | Olesen et al. |
| 2019/0009028 | A1 | 1/2019 | Jacobsen et al. |
| 2019/0009029 | A1 | 1/2019 | Fabricius et al. |
| 2020/0384207 | A1 | 12/2020 | Egesborg et al. |
| 2022/0152310 | A1 | 5/2022 | Pedersen et al. |
| 2022/0288316 | A1 | 9/2022 | Olesen et al. |
| 2023/0016657 | A1 | 1/2023 | Pedersen et al. |
| 2023/0072178 | A1 | 3/2023 | Jacobsen et al. |
| 2023/0263961 | A1 | 8/2023 | Egesborg et al. |
| 2023/0270945 | A1 | 8/2023 | Fabricius et al. |
| 2023/0338659 | A1 | 10/2023 | Olesen et al. |
| 2024/0082494 | A1 | 3/2024 | Jensen et al. |
| 2024/0165336 | A1 | 5/2024 | Pedersen et al. |

FOREIGN PATENT DOCUMENTS

| | | |
|---|---|---|
| CN | 102740907 | 10/2012 |
| CN | 103813820 | 5/2014 |
| CN | 105492047 | 4/2016 |
| EP | 2656865 | 10/2013 |
| EP | 2675500 | 12/2013 |
| EP | 2777731 | 9/2014 |
| EP | 2923715 | 9/2015 |
| GB | 2356349 | 5/2001 |
| GB | 2506918 | 4/2014 |
| JP | H11513586 | 11/1999 |
| JP | 2000-513973 | 10/2000 |
| JP | 2001-513371 | 9/2001 |
| JP | 2005-503202 | 2/2005 |
| JP | 2005-080832 | 3/2005 |
| JP | 2007-500531 | 1/2007 |
| JP | 2008-531235 | 8/2008 |
| JP | 2009-279438 | 12/2009 |
| JP | 2010-506681 | 3/2010 |
| JP | 2010-510011 | 4/2010 |
| JP | 2010-523181 | 7/2010 |
| JP | 2011-507668 | 3/2011 |
| JP | 2011-521744 | 7/2011 |
| JP | 2011-240159 | 12/2011 |
| JP | 2012-505066 | 3/2012 |
| JP | 2012-066767 | 4/2012 |
| JP | 2012-516737 | 7/2012 |
| JP | 2012-519028 A | 8/2012 |
| JP | 2013-506444 | 2/2013 |
| JP | 2013-069305 | 4/2013 |
| JP | 2013-075154 | 4/2013 |
| JP | 2013-537844 | 10/2013 |
| JP | 2014-500746 | 1/2014 |
| JP | 2014-502890 | 2/2014 |
| JP | 2014-503279 | 2/2014 |
| JP | 2014-506159 | 3/2014 |
| JP | 2014-507223 | 3/2014 |
| JP | 2014-515941 | 7/2014 |
| JP | 2014-516700 | 7/2014 |

(56) References Cited

FOREIGN PATENT DOCUMENTS

| | | |
|---|---|---|
| JP | 2014-516702 | 7/2014 |
| JP | 2014-521113 | 8/2014 |
| JP | 2014-4528787 | 10/2014 |
| JP | 2015-521920 | 8/2015 |
| JP | 2015-163208 | 9/2015 |
| JP | 2016-208611 | 12/2016 |
| KR | 10-2015-0125701 | 11/2015 |
| KR | B-10-1666755 | 10/2016 |
| KR | 10-2017-0013870 | 2/2017 |
| PT | 3397321 | 10/2022 |
| RU | 2014-120469 | 11/2015 |
| WO | WO 2002/051471 | 7/2002 |
| WO | WO 2005/102416 | 11/2005 |
| WO | WO 2006/116997 | 11/2006 |
| WO | WO 2008/062025 | 5/2008 |
| WO | WO 2006/059597 | 6/2008 |
| WO | WO 2010/098927 | 9/2010 |
| WO | WO 2010/098931 | 9/2010 |
| WO | WO 2012/112347 | 8/2012 |
| WO | WO 2010/100883 | 9/2012 |
| WO | WO 2012/160157 | 11/2012 |
| WO | WO 2013/065055 | 5/2013 |
| WO | WO 2013/138830 | 9/2013 |
| WO | WO 2014/008393 | 1/2014 |
| WO | WO 2012/066767 | 5/2014 |
| WO | WO 2014/144096 | 9/2014 |
| WO | WO 2014/166915 | 10/2014 |
| WO | WO 2014/168205 | 10/2014 |
| WO | WO 2014/187812 | 11/2014 |
| WO | WO 2014/187813 | 11/2014 |
| WO | WO 2015/006430 | 1/2015 |
| WO | WO 2013/069305 | 4/2015 |
| WO | WO 2015/055640 | 4/2015 |
| WO | WO 2015/055642 | 4/2015 |
| WO | WO 2015/115326 | 8/2015 |
| WO | WO 2015/187797 | 12/2015 |
| WO | WO 2016/005421 | 1/2016 |
| WO | WO 2016/033507 | 3/2016 |
| WO | WO 2016/098060 | 6/2016 |
| WO | WO 2014/091765 | 1/2017 |
| WO | WO 2017/009724 | 1/2017 |
| WO | WO 2017/114906 | 7/2017 |
| WO | WO 2017/114907 | 7/2017 |
| WO | WO 2017/114908 | 7/2017 |
| WO | WO 2017/114909 | 7/2017 |
| WO | WO 2017/114910 | 7/2017 |
| WO | WO 2017/114911 | 7/2017 |
| WO | WO 2017/114912 | 7/2017 |
| WO | WO 2018/215516 | 11/2018 |
| WO | WO 2019/002534 | 1/2019 |
| WO | WO 2020/176319 | 9/2020 |
| WO | WO 2023/052487 | 4/2023 |

OTHER PUBLICATIONS

English translation of Office Action issued in Japanese Application No. 2021-116315, dated Sep. 2, 2022.
English translation of Office Action issued in Korean Application No. 10-2020-7000564, dated Oct. 17, 2022.
Office Action in Canadian Application No. 3,006,626, dated Dec. 19, 2022, in 5 pages.
Office Action in Canadian Application No. 3,006,616, dated Dec. 19, 2022, in 3 pages.
Office Action in Canadian Application No. 3,006,638, dated Jan. 17, 2023, in 4 pages.
Office Action in Canadian Application No. 3,006,627, dated Dec. 30, 2022, in 5 pages.
Office Action in Canadian Application No. 3,006,643, dated Jan. 4, 2023, in 7 pages.
Office Action in Canadian Application No. 3,006,622, dated Jan. 4, 2023, in 4 pages.
English Translation of Office Action dated Jun. 3, 2021, in Corresponding Chinese Application No. 201880043795.0.
English Translation of Office Action dated Jul. 9, 2021, in corresponding Russian Application No. 2019140269.
English Translation of Office Action dated Jul. 30, 2021, in corresponding Russian Application No. 2020103216.
English Translation of Office Action dated Jun. 10, 2021, in corresponding Chinese Application No. 201880033657.4.
English translation of Office Action issued in Japanese Application No. 2019-565323, dated Jan. 5, 2022.
English translation of Office Action issued in Japanese Application No. 2019-570894, dated Jan. 13, 2022.
English translation of Office Action issued in Chinese Application No. 201880033657, dated Feb. 23, 2022.
European Search Report for EP 15203132.4, dated Jun. 29, 2016.
European Search Report for EP 15203137.3, dated Jul. 1, 2016.
Partial European Search Report for EP15203168.8, dated Sep. 16, 2016.
International Search Report for PCT/EP2016/082861, dated Mar. 22, 2017.
International Preliminary Report on Patentability for PCT/EP2016/082861, mailed Jul. 12, 2018.
International Search Report for PCT/EP2016/082856, mailed on Mar. 28, 2017.
International Preliminary Report on Patentability for PCT/EP2016/082856, mailed Jul. 12, 2018.
International Search Report for PCT/EP2016/082860, mailed on May 3, 2017.
International Preliminary Report on Patentability for PCT/EP2016/082860, mailed on Jul. 12, 2018.
International Search Report for PCT/EP2016/082858, mailed Mar. 24, 2017.
International Preliminary Report on Patentability for PCT/EP2016/082858, mailed on Jul. 12, 2018.
International Search Report for PCT/EP2016/082855, mailed Mar. 24, 2017.
International Preliminary Report on Patentability for PCT/EP2016/082855, mailed on Jul. 12, 2018.
International Search Report for PCT/EP2016/082857, mailed May 12, 2017.
International Preliminary Report on Patentability for PCT/EP2016/082857, mailed on Jul. 12, 2018.
International Search Report for PCT/EP2016/082859, mailed on Apr. 10, 2017.
International Preliminary Report on Patentability for PCT/EP2016/082859, mailed on Jul. 12, 2018.
International Search Report for PCT/EP2018/063460, mailed on Mar. 7, 2018.
International Preliminary Report on Patentability for PCT/EP2018/063460, mailed on Dec. 5, 2019.
International Search Report for PCT/EP2018/067532, mailed on Sep. 25, 2018.
International Preliminary Report on Patentability for PCT/EP2018/067532, mailed on Jan. 9, 2020.
European Search Report for EP 18733296.0, dated Feb. 1, 2023, in 5 pages.
Office Action in New Zealand Application No. 742523, dated Feb. 27, 2023, in 3 pages.
Office Action in New Zealand Application No. 742538, dated Mar. 8, 2023, in 9 pages.
Office Action in New Zealand Application No. 742526, dated Mar. 13, 2023, in 8 pages.
Office Action in Australian Application No. 2018-294519, dated Mar. 10, 2023, in 3 pages.
English translation of Office Action issued in Japanese Application No. JP 2022-074131, dated Apr. 28, 2023, in 2 pages.
English translation of Office Action issued in Japanese Application No. JP 2021-116315, dated Apr. 25, 2023, in 3 pages.
Office Action in New Zealand Application No. 742526, dated Jul. 6, 2023, in 10 pages.
Office Action in Canadian Application No. 3,064,056, dated Jul. 11, 2023, in 5 pages.
English translation of Office Action issued in Japanese Application No. JP 2023-021789, dated Nov. 7, 2023, in 5 pages.

(56) References Cited

OTHER PUBLICATIONS

Office Action with English translation in Korean application No. 10-2023-7043623, dated Apr. 18, 2024, in 12 pages.
Hearing Notice dispatched on Dec. 29, 2023 in India Patent Application No. 201947041763.

\* cited by examiner

AUTO INJECTOR WITH TEMPERATURE CONTROL

CROSS REFERENCE TO RELATED APPLICATIONS

This application is a continuation of U.S. patent application Ser. No. 16/060,600, filed on Jun. 8, 2018, which is a U.S. National Phase Application of PCT International Application Number PCT/EP2016/082857, filed on Dec. 29, 2016, designating the United States of America and published in the English language, which is an International Application of and claims the benefit of priority to European Patent Application No. 15203168.8, filed on Dec. 30, 2015, and European Patent Application No. 16190461.0, filed on Sep. 23, 2016. The disclosures of the above-referenced applications are hereby expressly incorporated by reference in their entireties.

FIELD

The present disclosure relates to an auto injector, such as an electronic auto injector, a cartridge for an auto injector, a system comprising an auto injector and a cartridge, and a method for operating an auto injector.

BACKGROUND

Hypodermic syringes are widely used to deliver fluids to the body. It is known to have hypodermic syringes applicable for manual operation. However, auto injectors, such as electronic auto injectors, have been developed and are widely used to aid the administering of fluid or medicaments to the body.

To avoid relying on users correctly performing certain tasks, it is of increasing interest that the auto injector automatically carries out as much as possible of the injection process. Especially, when administering of the medicament requires several steps, such as if medicament needs to be mixed prior to injection, it may be beneficial to automate the process of preparing and administering the fluid, such as a medicament.

Furthermore, it may be advantageous to incorporate sensors into such device, to allow for a precise control in varying circumstances.

SUMMARY

There is a need for an auto injector, such as an electronic auto injector, with an improved automation of preparing and administering the medicament. The present disclosure provides an auto injector, a cartridge, a system, and a method improving the preparation and administering of medicament with an auto injector.

Accordingly, an auto injector for preparing and/or administering a medicament, such as a medicament from a cartridge is disclosed.

The auto injector comprises: a housing; a cartridge receiver; a drive module; a temperature sensor; and a processing unit.

The cartridge receiver is configured to receive a cartridge, such as a cartridge comprising a first stopper and a cartridge compartment containing the medicament. The cartridge compartment has a first cartridge subcompartment containing a first medicament component of the medicament and a second cartridge subcompartment containing a second medicament component of the medicament.

The drive module is coupled to move a plunger rod between a retracted plunger rod position and an extended plunger rod position. The plunger rod is configured to move the first stopper.

The temperature sensor is configured to provide a temperature signal indicative of the temperature of the medicament in the cartridge, e.g. when the cartridge is received in the cartridge receiver.

The processing unit is coupled to the temperature sensor and the drive module. The processing unit is configured to: receive the temperature signal; control the drive module to move the plunger rod from a first plunger rod position to a mix plunger rod position; control the drive module to move the plunger rod from the mix plunger rod position to a second plunger rod position after a reconstitution time has elapsed since completion of movement of the plunger rod to the mix plunger rod position.

The mix plunger rod position is selected to position the first stopper in a position wherein the first medicament component is mixed with the second medicament component.

The processing unit is further configured to control the drive module to move the plunger rod from the first plunger rod position to the mix plunger rod position with a mix plunger rod speed. The mix plunger rod speed may be constant speed or a varying speed.

The movement from the first plunger rod position to the mix plunger rod position is based on the temperature signal. For example, the processing unit may be configured to control the drive module to move the plunger rod from the first plunger rod position to the mix plunger rod position based on the temperature signal.

Also disclosed is a cartridge for an auto injector, such as the disclosed auto injector. The cartridge comprises a first stopper and a cartridge compartment containing the medicament. The cartridge compartment has a first cartridge subcompartment containing a first medicament component of the medicament and a second cartridge subcompartment containing a second medicament component of the medicament. The cartridge may have a first cartridge end and a second cartridge end and have a cartridge outlet at the first cartridge end. The cartridge is configured to be received by a cartridge receiver of an auto injector, such as a cartridge receiver of the disclosed auto injector, e.g. by insertion of the second end of the cartridge through a cartridge receiver opening of the auto injector.

Also disclosed is a system comprising an auto injector, such as the disclosed auto injector, and a cartridge, such as the disclosed cartridge.

Also disclosed is a method for operating an auto injector, such as the disclosed auto injector, e.g. an auto injector comprising a cartridge receiver configured to receive a cartridge, such as the disclosed cartridge, e.g. a cartridge comprising a first stopper and a cartridge compartment containing the medicament, the cartridge compartment having a first cartridge subcompartment containing a first medicament component of the medicament and a second cartridge subcompartment containing a second medicament component of the medicament. The auto injector may further comprise a plunger rod configured to move the first stopper, and a temperature sensor.

The method comprises: receiving the temperature signal from the temperature sensor indicative of the temperature of the medicament; moving the plunger rod from a first plunger rod position to a mix plunger rod position with a mix plunger rod speed, wherein the mix plunger rod position is selected to position the first stopper in a position wherein the first medicament component is mixed with the second medicament component, and wherein the movement from the first plunger rod position to the mix plunger rod position is based on the temperature signal; moving the plunger rod from the mix plunger rod position to a second plunger rod position after a reconstitution time has elapsed since completion of movement of the plunger rod to the mix plunger rod position.

The first plunger rod position may be a pre-mix plunger rod position. The pre-mix plunger rod position may be selected to position the first stopper in a position wherein fluid communication between the first cartridge subcompartment and the second cartridge subcompartment is not yet established. Alternatively, the first plunger rod position may be a retracted plunger rod position, e.g. an initial plunger rod position.

The second plunger rod position may be a prime plunger rod position. The prime plunger rod position may be selected to position the first stopper in a position wherein air in the cartridge compartment is reduced to an amount appropriate for injection. Alternatively, the second plunger rod position may be an injection plunger rod position. The second plunger rod position may be the extended plunger rod position.

The method may further comprise receiving a trigger event; and moving the plunger rod to an injection plunger rod position following reception of the trigger event, e.g. after completion of movement of the plunger rod to the second plunger rod position.

The trigger event may, for example, be an effect of a push of a button, an effect of an elapsed timeout, and/or an effect of a predetermined user behaviour. The trigger event may be indicative of the auto injector being pressed against the injection site.

It is an advantage of the present disclosure that the steps involved in preparing and/or administering a medicament are increasingly automated. It is further an advantage that such increased automation provides for increased safety in preparing and/or administering the medicament.

It is a further advantage of the present disclosure that an auto injector may be provided which is easier to use, and reduce the risk of erroneous administering of a medicament.

It is a further advantage of the present disclosure that an auto injector may be operated according to the temperature, such as the temperature of the medicament, e.g. to increase precision in the operation of the auto injector.

Thus, it is a further advantage of the present disclosure, that patient safety is increased.

It is envisaged that any embodiments or elements as described in connection with any one aspect may be used with any other aspects or embodiments, mutatis mutandis.

The cartridge may have a cartridge outlet at the first cartridge end. The cartridge may comprise a cartridge back face, e.g. at the second cartridge end, such as opposite the cartridge outlet. The cartridge back face may comprise a cartridge back end opening. The cartridge back end opening may provide access for a plunger rod, such as the plunger rod of the auto injector, to the first stopper.

The cartridge compartment may contain the medicament. The cartridge outlet may be configured for fluid communication with the compartment, e.g. at the first cartridge end. The cartridge may be configured to expel medicament through the cartridge outlet. The cartridge outlet may be configured to be coupled with a needle, such as a hypodermic needle, to provide the medicament to be expelled through the needle.

The cartridge comprises a first stopper movable inside the cartridge compartment. The cartridge may comprise a second stopper movable inside the cartridge compartment. The second stopper may be between the first stopper and the cartridge outlet. The cartridge may comprise a third stopper movable inside the cartridge compartment. The third stopper may be between the second stopper and the cartridge outlet. The first stopper, the second stopper, and/or the third stopper may be movable inside the cartridge compartment towards the cartridge outlet, e.g. in a first stopper direction, such as towards the first cartridge end. For example, the medicament may be expelled through the cartridge outlet upon movement of the first stopper, the second stopper, and/or the third stopper, e.g. in the first stopper direction and/or towards the cartridge outlet.

The cartridge may be a dual-chamber cartridge. The cartridge compartment may have a first cartridge subcompartment and a second cartridge subcompartment. The first cartridge subcompartment may be between the first stopper and the second stopper. The second cartridge subcompartment may be between the second stopper and the cartridge outlet and/or the third stopper.

The first cartridge subcompartment may contain a first medicament component of the medicament. The second cartridge subcompartment may contain a second medicament component of the medicament. Each of the first medicament component and/or second medicament component may be a powder composition, a fluid, a liquid, a gel, a gas, and/or any combination thereof. The first medicament component and/or the second medicament component may be solute, such as a powder composition. The first medicament component and/or the second medicament component may be a solvent, such as a fluid composition, such as a liquid composition. The second medicament component may be a powder composition and the first medicament component may be a fluid composition, e.g. water or ethanol or saline solution or buffer solution or preservative solution. The second medicament component may be a solute. The first medicament component may be a solvent. It is envisaged that the medicament may be any medicament being injectable via a hypodermic needle, for example after reconstitution of the medicament. The medicament may be a growth hormone. The medicament may be human growth hormone. The medicament may be a depot version, such as a long-acting version, of human growth hormone. The second medicament component may be a powder composition of human growth hormone.

The cartridge may have a bypass section providing fluid communication between the first cartridge subcompartment and the second cartridge subcompartment, e.g. when the second stopper is positioned in the bypass section. The cartridge may have a plurality of bypass sections providing fluid communication between neighbouring cartridge subcompartments, e.g. when a stopper separating the neighbouring cartridge subcompartment is positioned in the bypass section.

The disclosed auto injector may be a reusable auto injector. A reusable auto injector may be especially useful when the cartridge comprises a plurality of subcompartments. For example an auto injector for a multi compartment or multi chamber cartridge may be more advanced, and therefore it may be beneficial to allow the auto injector to be used more than one time. For example, the auto injector may provide automated processes for mixing medicament components, such as for mixing medicament components initially provided in different subcompartments of the cartridge.

The cartridge may be comprised as part of a cartridge assembly. The cartridge assembly may comprise the cartridge. Additionally, the cartridge assembly may comprise a needle, such as a needle assembly comprising a needle, a needle cover, a cartridge holder, and/or a cartridge code feature.

The cartridge assembly may comprise the needle, such as the needle assembly comprising the needle. The needle assembly may comprise a needle cover and/or a needle hub. The cartridge assembly may comprise a cartridge holder. The cartridge holder may be configured to engage with the needle assembly. The cartridge holder may provide for attachment of the needle assembly to the cartridge.

The cartridge may comprise a cartridge code feature and/or the cartridge assembly may comprise the cartridge and the cartridge code feature. The cartridge code feature may comprise one or more of a colour, a bar code, an RFID tag, an NFC tag, an identification number, and a QR code. For example, the cartridge code feature may comprise a colour and/or a sequence of colours. The cartridge code feature may be positioned surrounding or partly surrounding a part of the cartridge compartment wherein a stopper, such as the first stopper, is initially positioned. Such position of the cartridge code feature may increase readability of the cartridge code feature, e.g. since the stopper may form a background for the cartridge code feature. The stopper, such as the first stopper may be a light colour, such as light grey or white. The stopper, such as the first stopper, may be a dark colour, such as dark blue, dark grey, or black. The stopper may form a dark background for the cartridge code feature. The stopper, such as the first stopper, may reduce reflection of light, e.g. to further increase readability of the cartridge code feature.

The cartridge code feature may be positioned at a specific position on the cartridge, e.g. independently of the stopper(s), such as the first stopper. For example, the cartridge code feature may be positioned at a code distance from the second cartridge end. All cartridges may have their cartridge code features positioned at the same position, e.g. positioned at the code distance from the second cartridge end. Such uniform position of the cartridge code feature may decrease complexity, and decrease size, of the auto injector, as the cartridge code feature is read in the same position for all suitable cartridges.

The cartridge and the cartridge code feature may be manufactured as one element. For example, the cartridge code feature may be a certain form of the cartridge. Alternatively, the cartridge code feature may be attached to the cartridge, such as fastened, e.g. by glue, to the cartridge. For example, the cartridge code feature may be a colour code printed on the cartridge.

The cartridge code feature may be indicative of one or more cartridge specifications, such as medicament in the cartridge, concentration of medicament in the cartridge, viscosity of medicament in the cartridge, volume and/or mass of medicament in the cartridge, positions of stopper(s) in the cartridge compartment, etc. The cartridge code feature may be indicative of a position of the first stopper wherein air in the cartridge compartment is reduced, such as minimized and/or reduced to an amount appropriate for injection. The cartridge code feature may be indicative of the amount of medicament contained in the cartridge. The cartridge code feature may be indicative of a specific type of cartridge, such as an ID number of the specific type of cartridge. The auto injector, such as the processing unit of the auto injector, may be configured to determine one or more cartridge specifications based on an ID number, e.g. by table lookup. The cartridge code feature may be indicative of a suitable, such as optimal, speed of stopper movement, such as stopper movement in different phases of movement, such as during mixing, during air-shot, and/or injection. The cartridge code feature may be indicative of a suitable, such as optimal, speed of movement of the first stopper, such as speed of movement of the first stopper in different phases of movement, such as during mixing, during air-shot, and/or injection. The cartridge code feature may be indicative of time needed for optimal mixing of the first medicament component and the second medicament component. The cartridge code feature may be indicative of a suitable dwell time for the medicament, e.g. time to ensure that the medicament is distributed into the tissue, e.g. favourable time to wait after injection before retraction of the needle. The cartridge code feature may be indicative of amount of movement energy needed for optimal mixing of the first medicament component and the second medicament component. The cartridge code feature may be indicative of desired temperatures of the medicament, e.g. for mixing of the first medicament component and the second medicament component and/or for injection of the medicament.

The auto injector may be a front-loaded auto injector. The auto injector comprises a cartridge receiver configured to receive the cartridge. The cartridge receiver may be configured to receive a cartridge assembly comprising the cartridge. The cartridge assembly may comprise a cartridge holder. The cartridge receiver may have a cartridge receiver opening. The cartridge receiver may be configured to receive the cartridge by insertion of the cartridge, such as the second end of the cartridge, through the cartridge receiver opening. The cartridge may be inserted in a cartridge receiving direction. The cartridge receiving direction may be opposite the first stopper direction, e.g. when the cartridge is received in the cartridge receiver. The cartridge may be in a first angular position when inserted into the cartridge receiver. The cartridge may be retained in the cartridge receiver in a second angular position, e.g. after insertion of the cartridge in the cartridge receiver.

The cartridge receiver may be configured to receive a cartridge assembly comprising the cartridge and a cartridge holder. The cartridge assembly may be retained in the cartridge receiver by one or more cartridge retention members of the cartridge holder engaging with members of the cartridge receiver.

The cartridge and/or cartridge assembly may be lockable in the cartridge receiver, e.g. the cartridge and/or cartridge assembly may be locked in the cartridge receiver to prevent removal of the cartridge and/or cartridge assembly from the cartridge receiver. The cartridge and/or cartridge assembly may be locked in the cartridge receiver by movement of a plunger rod of the auto injector.

The auto injector may comprise a cartridge sensor. The cartridge receiver may comprise the cartridge sensor. The cartridge sensor may be configured to detect reception of the cartridge and/or cartridge assembly in the cartridge receiver. The cartridge sensor may provide a cartridge sensor signal indicative of whether the cartridge and/or cartridge assembly is received in the cartridge receiver. The cartridge sensor may provide a cartridge detection signal indicative of the cartridge and/or cartridge assembly being received in the cartridge receiver. The cartridge sensor signal may comprise the cartridge detection signal.

The auto injector may be an electronic auto injector. The auto injector may comprise a battery. The housing may accommodate the battery. The battery may be a rechargeable battery. For example, the battery may be a Li-ion battery or a NiCd battery or a NiMH battery. The battery may be configured to be charged by connection of a charger.

The auto injector comprises a drive module. The drive module may be coupled to move, such as actuate, such as advance, a plunger rod, such as between a retracted plunger rod position and an extended plunger rod position. Movement of the plunger rod may provide the cartridge and/or cartridge assembly to be locked in the cartridge receiver. For example, the cartridge and/or cartridge assembly may be locked in the cartridge receiver by advancement of the plunger rod from a retracted plunger rod position.

The drive module may comprise one or more electrical elements. The drive module may be configured to receive electrical power from the battery. The drive module may be electrically connected to the battery for receiving electrical power. The drive module may be accommodated by the housing. The drive module may comprise a motor, such as an electro-mechanical motor, such as a DC motor, e.g. a DC motor with or without brushes. The drive module may comprise a solenoid motor. The drive module may comprise a shape memory metal engine. The drive module may comprise an arrangement of springs configured to actuate the plunger rod. The drive module may comprise a pressurized gas configured to actuate the plunger rod.

The auto injector may comprise a plunger rod, such as the plunger rod movable by the drive module. The plunger rod may be configured to move a stopper, such as the first stopper of the cartridge. For example, when the plunger rod is moved towards an extended plunger rod position, such as from the first plunger rod position to the mix plunger rod position and/or from the mix plunger rod position to the second plunger rod position, the plunger rod may be configured to move the first stopper towards the cartridge outlet, such as to mix the two medicament components and/or to expel medicament from the cartridge compartment through the cartridge outlet and/or to expel air from the cartridge compartment through the cartridge outlet.

The plunger rod may be moved to the first plunger rod position, such as a pre-mix plunger rod position, such as towards the extended plunger rod position, such as from a retracted plunger rod position. The first plunger rod position may be a pre-mix plunger rod position. The pre-mix plunger rod position may be selected to position the first stopper in a position wherein fluid communication between the first cartridge subcompartment and the second cartridge subcompartment is not yet established.

The plunger rod may be moved to the mix plunger rod position, such as towards the extended plunger rod position, such as from the first plunger rod position. The mix plunger rod position may be a position wherein the first medicament component and the second medicament component are mixed, such as combined. The mix plunger rod position may be a position wherein the second stopper is positioned in the bypass section, such as to provide fluid communication between the first cartridge subcompartment and the second cartridge subcompartment.

The plunger rod may be moved to a second plunger rod position, such as towards the extended plunger rod position, such as from the mix plunger rod position. The second plunger rod position may be a prime plunger rod position. The prime plunger rod position may be selected to position the first stopper in a position wherein air has been expelled from the cartridge compartment. For example, the prime plunger rod position may be selected to position the first stopper in a position wherein air in the cartridge compartment is reduced, such as minimized and/or reduced to an amount appropriate for injection.

The plunger rod may be moved to an injection plunger rod position, such as towards the extended plunger rod position, such as from the second plunger rod position. The injection plunger rod position may be a position wherein the medicament has been expelled and/or injected from the cartridge compartment. For example, the injection plunger rod position may be selected to position the first stopper in a position wherein medicament in the cartridge compartment is reduced, such as minimized, such as in a position close to the cartridge outlet. The injection plunger rod position may be the extended plunger rod position.

The plunger rod may be moved towards a retracted plunger rod position, e.g. to the retracted plunger rod position. For example, the plunger rod may be moved towards the retracted plunger rod position, e.g. to the retracted plunger rod position, after completion of injection, such as from the injection plunger rod position and/or the extended plunger rod position.

The processing unit may be configured to move the plunger rod to the mix plunger rod position, the second plunger rod position, the injection plunger rod position, the extended plunger rod position and/or the retracted plunger rod position.

The processing unit may be configured to receive a trigger event, and control the drive module to move the plunger rod to the injection plunger rod position following reception of the trigger event, such as after completion of movement of the plunger rod to a preceding plunger rod position, such as the second plunger rod position.

The auto injector may comprise an ejection sensor, such as a plunger rod position sensor. The ejection sensor may be configured to detect the ejection, such as the expelling, of medicament and/or air in the cartridge compartment. The ejection sensor may be configured to detect and/or determine the position of the plunger rod and/or the position of the first stopper. The ejection sensor may be configured to detect conditions indicative of the position of the plunger rod and/or the position of the first stopper. The ejection sensor may be configured to provide an ejection sensor signal. The ejection sensor signal may be indicative of the position of the plunger rod and/or the first stopper.

The ejection sensor may comprise a tachometer, e.g. a tachometer of the drive module. The tachometer may be configured to count the revolutions of the drive module, such as a motor of the drive module, such as the revolutions of the drive module from a set point, such as a point wherein the position of the plunger rod is known, such as the retracted plunger rod position of the plunger rod. The count of revolutions of the drive module may be used to determine the actual position of the plunger rod, such as the pre-mix plunger rod position, the mix plunger rod position, the prime plunger rod position, the injection plunger rod position, the extended plunger rod position and/or the retracted plunger rod position.

The processing unit may be coupled to the ejection sensor, such as to the tachometer. The processing unit may receive from the ejection sensor a first ejection sensor signal, such as a tachometer signal, indicative of the count of revolutions of the drive module. The processing unit may determine the position of the plunger rod based on the first ejection sensor signal. The processing unit may receive a second ejection sensor signal, e.g. from the ejection sensor, indicative of the plunger rod being in a known position, such as the retracted plunger rod position and/or the first plunger rod position. The processing unit may determine the position of the plunger rod based on the first ejection sensor signal and the second ejection sensor signal.

The cartridge may be lockable in the cartridge receiver, e.g. the cartridge may be locked in the cartridge receiver to prevent removal of the cartridge from the cartridge receiver. Movement of the plunger rod towards the extended plunger rod position may lock the cartridge in the cartridge receiver. For example, movement of the plunger rod to the mix plunger rod position may lock the cartridge in the cartridge receiver. Movement of the plunger rod towards the retracted plunger rod position may unlock the cartridge from the cartridge receiver. For example, movement of the plunger rod to the retracted plunger rod position may unlock the cartridge in the cartridge receiver. The cartridge may be locked in the cartridge receiver when the plunger rod is not in the retracted plunger rod position and/or close to the retracted plunger rod position.

Coupling the position of the plunger rod with the locking of the cartridge in the cartridge receiver may provide the advantage that the release of the cartridge may be restricted or prevented when the auto injector is active.

The auto injector may comprise an orientation sensor. The orientation sensor may be configured to provide an orientation signal indicative of the orientation of the cartridge, e.g. when the cartridge is received in the cartridge receiver. The orientation signal may be indicative of the orientation of the cartridge relative to gravity, such as relative to the direction of gravity. The orientation signal may be an acceleration signal, e.g. a tri-axial acceleration signal. The orientation signal may comprise acceleration data, e.g. acceleration data in three dimensions. The orientation signal may comprise acceleration data indicative of acceleration of the device.

The orientation sensor may be configured to detect an orientation of the cartridge and/or an orientation indicative of the orientation of the cartridge, such as an orientation of the auto injector. The detected orientation may be relative to gravity, such as relative to the direction of gravity. The orientation sensor may be configured to detect the direction of gravity, and/or if the direction of gravity is within a certain range of a predetermined direction. The orientation sensor may comprise an accelerometer. The orientation sensor may comprise a plurality of accelerometers, such as three accelerometers, such as three accelerometers arranged to detect acceleration in three dimensions, such as a three-dimensional accelerometer. The orientation sensor may comprise a tilt sensor, a tri-axial accelerometer, a single axis accelerometer, a magnetometer and/or any combination thereof, and the orientation sensor may provide a measure of roll, pitch and azimuth, a measure of acceleration and/or tilt in one or more directions.

The orientation sensor may be configured to provide dynamic signals, e.g. linear acceleration and/or velocity and/or positional location and/or additional rotational acceleration and/or rotational velocity in one, two or three dimensions. The orientation sensor may be configured to provide full inertial sensing for the position and/or movement of the device. The processing unit may be configured to transform motional sensor signals, such as the orientation signal, from one domain into another domain, e.g. integration over time of an acceleration signal to derive a velocity signal and/or integration over time to derive a position signal from a velocity signal etc.

The orientation sensor may be configured to detect if the cartridge is in a predetermined orientation. The orientation sensor may be configured to detect if the orientation of the auto injector is indicative of the cartridge being in the predetermined orientation. The predetermined orientation may be a vertical orientation. The predetermined orientation may be an orientation within 45 degrees of vertical, such as within 30 degrees of vertical. The predetermined orientation may be an orientation wherein the cartridge is orientated such that a longitudinal axis of the cartridge is within 45 degrees of vertical, such as within 30 degrees of vertical, and wherein the cartridge outlet is above the cartridge compartment, such as in a vertical position above the cartridge compartment.

The processing unit may be coupled to the orientation sensor. The processing unit may be configured to receive the orientation signal, e.g. indicative of the orientation of the cartridge, e.g. when the cartridge is received in the cartridge receiver, and/or indicative of the orientation of the auto injector.

Movement of the plunger rod to the mix plunger rod position and/or to the second plunger rod position and/or to the injection plunger rod position may be based on the orientation of the cartridge, e.g. on the orientation signal. For example, movement of the plunger rod from the first plunger rod position to the mix plunger rod position may be based on the orientation signal.

For example, movement of the plunger rod to the mix plunger rod position and/or to the second plunger rod position and/or to the injection plunger rod position may require that a tilt angle between vertical and a longitudinal axis extending along the cartridge is within 45 degrees, such as within 30 degrees, and/or that the cartridge outlet is in a vertical position above the cartridge compartment.

Control of the drive module to move the plunger rod to the mix plunger rod position and/or to the prime plunger rod position and/or to the injection plunger rod position may be based on the orientation of the cartridge, e.g. on the orientation signal.

The processing unit may be configured to control the drive module based on the orientation signal. For example, the processing unit may be configured to control the drive module to move the plunger rod to the mix plunger rod position and/or to the second plunger rod position and/or to the injection plunger rod position based on the orientation signal. For example, the processing unit may be configured to control the drive module to move the plunger rod to the mix plunger rod position and/or to the second plunger rod position and/or to the injection plunger rod position only if the orientation signal indicates that a tilt angle between vertical and a longitudinal axis extending along the cartridge is within 45 degrees, such as within 30 degrees, of vertical, and/or if the cartridge outlet is in a vertical position above the cartridge compartment.

A first movement parameter may be determined, e.g. based on the orientation signal. The processing unit may be configured to determine the first movement parameter. The first movement parameter may be based on cumulative movement of the auto injector. The first movement parameter may be indicative of an amount of movement of the auto injector during a set period of time, such as since completion of movement of the plunger rod to the mix plunger rod position, and/or a preceding predetermined time, such as the preceding 1 second. The first movement parameter may be based on a cumulative measure of the orientation signal over time, e.g. since completion of movement of the plunger rod to the mix plunger rod position, and/or a preceding predetermined time, such as the preceding 1 second. The first movement parameter may be indicative of the device being shaken. Shaking the device while the two medicament components are mixing may provide excess foaming of the medicament. Excess foaming of the medicament may necessitate an increased reconstitution time. To prevent foaming, the speed of movement of the plunger rod may be adjusted, e.g. decreased if shaking the device is detected. Conversely, shaking the device gently might speed up the reconstitution without foaming thereby decreasing the necessary reconstitution time. Thus, the amount of shaking may influence the determined reconstitution time.

Alternatively or additionally, the first movement parameter may be indicative of the auto injector being rotated, e.g. from one vertical orientation, such as wherein a first end of the auto injector, such as a distal end of the auto injector, points substantially upwards, to an inverted orientation wherein the first end of the auto injector points substantially downwards. The first movement parameter may be indicative of number of inversions of the auto injector. The processing unit may be configured to detect and/or count number of inversions. An inversion may comprise inversion of the auto injector from an orientation wherein the first end of the auto injector points substantially upwards, to an inverted orientation wherein the first end of the auto injector points substantially downwards. For example, an inversion may comprise inversion of the auto injector from an orientation wherein the first end of the auto injector points within 45 degrees of upwards, to an inverted orientation wherein the first end of the auto injector points within 45 degrees of downwards. Alternatively or additionally, an inversion may comprise inversion of the auto injector from an orientation wherein the first end of the auto injector points substantially downwards, to an inverted orientation wherein the first end of the auto injector points substantially upwards. For example, an inversion may comprise inversion of the auto injector from an orientation wherein the first end of the auto injector points within 45 degrees of downwards, to an inverted orientation wherein the first end of the auto injector points within 45 degrees of upwards The processing unit may be configured to provide feedback, such as via the user interface of the auto injector, when a predefined number of inversions have been completed. The reconstitution time may be based on the first movement parameter, such as if the predefined number of inversions have been completed. The predefined number of inversions may be based on an amount of motion energy applied to the mixed drug during reconstitution, e.g. the predefined number of inversions may be correlated with the amount of motion energy applied to the mixed drug during reconstitution. The predefined number of inversions may be between 1 and 10, such as between 3 and 7, such as 5. The predefined number of inversions may be based on the cartridge code feature, such as on a code signal indicative of the cartridge code feature. Alternatively or additionally, the predefined number of inversions may be based on temperature of the medicament, such as a temperature signal indicative of the temperature of the medicament.

The first movement parameter may be indicative of a combined rotation between opposite vertical orientations in combination with the angular speed of rotation and/or a waiting period/delay between such inversions. The processing unit may, e.g. in addition to counting number of inversions, measure rotational acceleration of the auto injector. The processing unit may estimate force and energy acting on the drug to be reconstituted, e.g. based on the measure of rotational acceleration of the auto injector and/or counting number of inversions. The processing unit may provide feedback, e.g. via the user interface, when a predefined amount of energy has been applied to the auto injector and/or the cartridge.

Alternatively or additionally, it may be monitored that the acceleration does not exceed a predefined upper threshold. The predefined upper threshold may be indicative of accelerations known to be associated with risk of foaming. For example, accelerations above the predefined upper threshold may be known to be associated with risk of foaming.

The total amount of energy applied to the auto injector, such as based on the measure of rotational acceleration of the auto injector and/or counting number of inversions, may be assessed continuously to give real-time instructions e.g. to a user performing such movement, if the energy level is considered too low, e.g. below a predefined lower threshold, and/or if the energy level is considered to high, e.g. above a predefined upper threshold. The predefined lower threshold may be an energy level where the movement is considered to have no effect in speeding up reconstitution. The predefined upper threshold may be an energy level where the movement is considered to increase the risk of foaming.

The first movement parameter may be indicative of a frequency of movement of the auto injector, such as number of inversions per second.

The reconstitution time may be based on the first movement parameter, such as if the first movement parameter is indicative of a frequency above a frequency threshold. The frequency threshold may be between 0.3-1.2 Hz, such as between 0.5-0.9 Hz, such as 0.7 Hz. The frequency threshold may be based on the cartridge code feature, such as on a code signal indicative of the cartridge code feature. Alternatively or additionally, the frequency threshold may be based on temperature of the medicament, such as a temperature signal indicative of the temperature of the medicament.

The reconstitution time may be based on the first movement parameter, such as if the predefined number of inversions have been completed, such as if the predefined number of inversions have been completed with a frequency above the frequency threshold. For example, the reconstitution time may be based on the predefined number of inversions being completed at a frequency above the frequency threshold, such as 5 inversions being completed with a frequency of 0.5 Hz or more.

The auto injector, e.g. the cartridge receiver, may be configured to receive a cartridge assembly comprising the cartridge and a cartridge code feature.

The auto injector may comprise a code sensor. The code sensor may be configured to read a cartridge code feature, such as the cartridge code feature of the cartridge and/or the cartridge assembly e.g. indicative of one or more cartridge specifications. The code sensor may be configured to provide a code signal indicative of the cartridge code feature.

The processing unit may be coupled to the code sensor. The processing unit may be configured to receive the code signal. The processing unit may be configured to receive from the code sensor a code signal indicative of the cartridge code feature. The movement of the plunger rod, such as the movement from the first plunger rod position to the mix plunger rod position, may be based on the code signal.

The processing unit may be configured to determine an unauthorized cartridge, such as a counterfeit cartridge and/or a used cartridge, and/or a tampered cartridge, and/or a cartridge containing a wrong dose, and/or a cartridge containing a wrong medicament, based on the code signal.

The code sensor may comprise an optical sensor. The code sensor may comprise an optical sensor comprising a transmitter and a receiver, such as a light transmitter and a light receiver. The code sensor may be configured to read the cartridge code feature. The code sensor may be configured to read colour codes, bar codes, RFID tags, NFC tags, identification numbers, QR codes, and/or any combination hereof.

Movement of the plunger rod, such as positions, speed and/or delays, may be based on the code signal. For example, movement of the plunger rod to the mix plunger rod position and/or the second plunger rod position and/or the injection plunger rod position, may be based on the cartridge code feature, e.g. on the code signal. For example, control of the drive module to move the plunger rod to the mix plunger rod position and/or to the second plunger rod position may be based on the code signal.

The processing unit may be configured to control the drive module based on the code signal. For example, the processing unit may be configured to control the drive module to move the plunger rod to the mix plunger rod position and/or to the second plunger rod position based on the code signal.

Basing the movement of the plunger rod on cartridge specification, e.g. on the code signal, provides that the plunger rod movement may be optimized to several types of cartridges. For example, the air-shot may be performed with reduced or no expelling of medicament, thereby increasing dosage accuracy and/or reducing patient discomfort, e.g. even with different cartridges. Additionally or alternatively, the mixing procedure may be performed with reduced foaming by knowing the specifications of the cartridge.

Basing the movement of the plunger rod on cartridge specification, e.g. on the code signal, provides that the plunger rod movement may be optimized to several types of cartridges. For example, the plunger rod may be kept in a mix plunger rod position for a time depending on the cartridge specification following detection of the cartridge being received in the cartridge receiver and reception of the first input signal thereby ensuring appropriate mixing and/or reducing patient discomfort, e.g. even with different cartridges.

The auto injector may comprise a resistance sensor. The resistance sensor may be configured to provide a resistance signal. The resistance signal may be indicative of resistance against movement of the plunger rod. The processing unit may be coupled to the resistance sensor. The processing unit may be configured to receive the resistance signal.

The resistance signal may be indicative of resistance against movement of the plunger rod in one direction, such as movement towards the extended plunger rod position. For example, the resistance signal may be indicative of the force necessary to move the plunger rod, e.g. towards the extended plunger rod position.

The resistance sensor may be configured to determine electrical power consumed by the drive module, e.g. by measuring electrical resistance, electrical current, and/or electrical voltage of the drive module and/or a combination thereof. The resistance sensor may comprise an electrical resistance sensor, an electrical current sensor, and/or an electrical voltage sensor. The drive module may comprise the resistance sensor.

The resistance sensor may be configured to measure pressure and/or force applied to a plunger rod front end of the plunger rod. The plunger rod front end may be configured to engage with the first stopper of the cartridge. The resistance sensor may be configured to measure pressure and/or force between the plunger rod and the stopper. For example, the resistance sensor may comprise a pressure transducer and/or a force transducer on the plunger rod front end. The plunger rod may comprise the resistance sensor.

Movement of the plunger rod may be based on the resistance signal. For example, movement of the plunger rod to the mix plunger rod position and/or the second plunger rod position and/or the injection plunger rod position, may be based on resistance against movement of the plunger rod, e.g. on the resistance signal. For example, control of the drive module to move the plunger rod to the mix plunger rod position may be based on the resistance signal. The processing unit may be configured to control the drive module based on the resistance signal. For example, the processing unit may be configured to control the drive module to move the plunger rod to the mix plunger rod position based on the resistance signal.

The auto injector may comprise a temperature sensor. The temperature sensor may be configured to provide a temperature signal, such as a temperature signal indicative of the temperature of the auto injector and/or of the cartridge and/or of the medicament, such as the temperature of the medicament in the cartridge, e.g. when the cartridge is received in the cartridge receiver. The temperature sensor may comprise an infrared sensor, such as an infrared optical sensor. The temperature sensor and the code sensor may utilize a common optical sensor, such as a common optical sensor. Thus, the optical sensor, such as an infrared optical sensor may be used both to sense temperature and read the cartridge code feature.

The processing unit may be coupled to the temperature sensor. The processing unit may be configured to receive the temperature signal.

Movement of the plunger rod to the mix plunger rod position and/or to the second plunger rod position and/or to the injection plunger rod position may be based on the temperature of the auto injector and/or of the cartridge and/or of the medicament. Movement of the plunger rod to the mix plunger rod position and/or to the second plunger rod position and/or to the injection plunger rod position may be based on the temperature signal.

The auto injector, such as the processing unit, may be configured to control the drive module based on the temperature signal. For example, the processing unit may be configured to control the drive module to move the plunger rod to the mix plunger rod position and/or to the prime plunger rod position and/or to the injection plunger rod position based on the temperature signal.

The auto injector may comprise a temperature control unit. The temperature control unit may be configured to alter the temperature of the cartridge, e.g. when the cartridge is received in the cartridge receiver. The temperature control unit may be configured to raise and/or lower the temperature of the cartridge and/or of the medicament. The steps of the procedure being dependent on temperature may thereby be controlled, for example, in order to perform the steps faster.

The temperature control unit may comprise a heating element. The heating element may be configured to raise the temperature of the auto injector and/or of the cartridge and/or of the medicament. The heating element may be a resistive heating element. The heating element may be a light source, e.g. an infrared lamp. The heating element may be a dielectric heating element. The heating element may be a thermoelectric element, such as a Peltier element.

The temperature control unit may comprise a cooling element. The cooling element may be configured to lower the temperature of the auto injector and/or of the cartridge and/or of the medicament. The cooling element may be a thermoelectric element, such as a Peltier element.

The temperature control unit may comprise a thermoelectric element, such as a Peltier element. The thermoelectric element may be used to raise or lower the temperature, such as by use of the Peltier effect, such as to transfer heat from one side of the element to the other with consumption of electrical energy. The thermoelectric element may be used to raise or lower the temperature depending on the direction of the current.

The temperature control unit may comprise a contact element configured to be in contact with the cartridge, e.g. when the cartridge is received in the cartridge receiver. The temperature control unit may comprise a coil element. The coil element may be configured to surround an entire perimeter of the cartridge, e.g. when the cartridge is received in the cartridge receiver.

The auto injector may comprise an input device, such as a first input device. The first input device may be a button or a touch sensitive area or a microphone. The first input device may be configured to provide the first input signal. The first input signal may be indicative of a first user interaction with the first input device. The first input device may be configured to provide a second input signal. The second input signal may be indicative of a second user interaction with the first input device.

The processing unit may be coupled to the first input device. The processing unit may be configured to receive the first input signal and/or the second input signal. The processing unit may be configured to control the drive module to move the plunger rod to the mix plunger rod position only after receiving the first input signal. The processing unit may be configured to control the drive module to move the plunger rod to the second plunger rod position only after receiving the second input signal.

The auto injector may comprise a contact member. The contact member may be configured to be pressed against the injection site. The contact member may be movable between an extended contact member position and a retracted contact member position. The contact member may be biased towards the extended contact member position, e.g. by a contact member spring. The contact member may be configured to be moved towards the retracted contact member position, e.g. when pressed against the injection site. The contact member and/or a contact member sensor may be configured to provide a contact member signal indicative of position of the contact member. The auto injector and/or the contact member may comprise a contact member sensor configured to detect the position of the contact member. The contact member sensor may be configured to provide the contact member signal indicative of the contact member.

The contact member may be in a first contact member position, e.g. between the extended contact member position and the retracted contact member position. The contact member being in the first contact member position may indicate that the contact member is close to the retracted contact member position. The contact member being in the first contact member position may indicate that the contact member is pressed against the injection site. The contact member being in the first contact member position may indicate that a needle positioned on the cartridge is pressed sufficiently into the skin for injection of the medicament to start.

The processing unit may be coupled to the contact member. The processing unit may be configured to receive the contact member signal. The trigger event may comprise the contact member signal being indicative of the contact member being in a first contact member position. The contact member may be a trigger member.

A plunger rod position, such as the first plunger rod position, the mix plunger rod position, the second plunger rod position and/or the injection plunger rod position may be based on the temperature of the medicament, such as on the temperature signal. For example, the medicament may have slightly different volume at different temperatures, which may be accounted for by determining plunger rod positions based on the temperature of the medicament. For example, the processing unit may be configured to determine the plunger rod positions, such as the first plunger rod position, the mix plunger rod position, the second plunger rod position and/or the injection plunger rod position based on the temperature signal.

The plunger rod positions, such as the first plunger rod position, the mix plunger rod position, the second plunger rod position and/or the injection plunger rod position may be based on a cartridge specification, such as on the cartridge code feature, such as on the code signal. For example, the processing unit may be configured to determine the plunger rod positions, such as the first plunger rod position, the mix plunger rod position, the second plunger rod position and/or the injection plunger rod position based on the code signal.

The plunger rod positions, such as the first plunger rod position, the mix plunger rod position, the second plunger rod position and/or the injection plunger rod position may be based on orientation of the cartridge, such as on orientation signal. For example, the processing unit may be configured to determine the plunger rod positions, such as the first plunger rod position, the mix plunger rod position, the second plunger rod position and/or the injection plunger rod position based on the orientation signal.

The plunger rod positions, such as the first plunger rod position, the mix plunger rod position, the second plunger rod position and/or the injection plunger rod position may be based on shaking of the device, such as on the first movement parameter. For example, the processing unit may be configured to determine the plunger rod positions, such as the first plunger rod position, the mix plunger rod position, the second plunger rod position and/or the injection plunger rod position based on the first movement parameter.

The plunger rod positions, such as the first plunger rod position, the mix plunger rod position, the second plunger rod position and/or the injection plunger rod position may be based on resistance against movement of the plunger rod, such as on the resistance signal. For example, the processing unit may be configured to determine the plunger rod positions, such as the first plunger rod position, the mix plunger rod position, the second plunger rod position and/or the injection plunger rod position based on the resistance signal.

The processing unit may be configured to determine the plunger rod positions, such as the first plunger rod position, the mix plunger rod position, the second plunger rod position and/or the injection plunger rod position, based on the code signal and/or the temperature signal and/or the orientation signal and/or the first movement parameter and/or the resistance signal.

Movement of the plunger rod may comprise movement having a plunger rod speed, such as the mix plunger rod speed, a second plunger rod speed and/or an injection plunger rod speed. The plunger rod speed may be based on the position of the plunger rod. The plunger rod may be moved to the mix plunger rod position, such as from the first plunger rod position, with a mix plunger rod speed. The plunger rod may be moved to the second plunger rod position, such as from the mix plunger rod position, with a second plunger rod speed. The plunger rod may be moved to the injection plunger rod position, such as from the mix plunger rod position and/or from the second plunger rod position, with an injection plunger rod speed.

The plunger rod speed, such as the mix plunger rod speed, the second plunger rod speed, and/or the injection plunger rod speed may be constant. The plunger rod speed, such as the mix plunger rod speed, the second plunger rod speed, and/or the injection plunger rod speed may be varying, e.g. varying over time and/or over distance.

The mix-plunger rod speed may be between 1 mm/second and 3 mm/second, such as 1.7 mm/second.

The processing unit may be configured to control the drive module to move the plunger rod to the mix plunger rod position, such as from the first plunger rod position, with the mix plunger rod speed. The processing unit may be configured to control the drive module to move the plunger rod to the second plunger rod position, such as from the mix plunger rod position, with the second plunger rod speed. The processing unit may be configured to control the drive module to move the plunger rod to the injection plunger rod position, such as from the second plunger rod position, with the injection plunger rod speed.

The mix plunger rod speed, the second plunger rod speed, and/or the injection plunger rod speed, may be based on a cartridge specification, such as on the cartridge code feature, such as on the code signal. The processing unit may be configured to determine the mix plunger rod speed, the second plunger rod speed, and/or the injection plunger rod speed, based on the code signal.

The mix plunger rod speed, the second plunger rod speed, and/or the injection plunger rod speed, may be based on the temperature of the medicament, such as on the temperature signal. The processing unit may be configured to determine the mix plunger rod speed, the second plunger rod speed, and/or the injection plunger rod speed, based on the temperature signal.

The mix plunger rod speed, the second plunger rod speed, and/or the injection plunger rod speed, may be based on the orientation of the cartridge, such as on the orientation signal. The processing unit may be configured to determine the mix plunger rod speed, the second plunger rod speed, and/or the injection plunger rod speed, based on the orientation signal.

The mix plunger rod speed, the second plunger rod speed, and/or the injection plunger rod speed, may be based on the first movement parameter. The processing unit may be configured to determine the mix plunger rod speed, the second plunger rod speed, and/or the injection plunger rod speed, based on the first movement parameter.

The mix plunger rod speed, the second plunger rod speed, and/or the injection plunger rod speed, may be based on resistance against movement of the plunger rod, such as on the resistance signal. The processing unit may be configured to determine the mix plunger rod speed, the second plunger rod speed, and/or the injection plunger rod speed, based on the resistance signal.

The processing unit may be configured to determine the mix plunger rod speed, the second plunger rod speed, and/or the injection plunger rod speed, based on the code signal and/or the temperature signal and/or the orientation signal and/or the first movement parameter and/or the resistance signal.

Movements of the plunger rod, such as movement to the mix plunger rod position, to the second plunger rod position, to the injection plunger rod position, may be preceded by one or more elapsed time, such as delays. For example, movement of the plunger rod to the second plunger rod position may require that a reconstitution time has elapsed since completion of the movement of the plunger rod to the mix plunger rod position. The reconstitution time may be chosen to allow sufficient time to ensure that the medicament is reconstituted, e.g. that the first medicament component and second medicament component has been sufficiently mixed, such as dissolved.

In some circumstances the reconstitution time may be very small. The reconstitution time may be less than 10 seconds, such as less than 5 seconds, such as less than 1 second. Alternatively, the reconstitution time may be more than 1 second, such as more than 10 seconds, such as more than 1 minute, such as more than 5 minutes.

The reconstitution time may be between 1-10 minutes, such as between 2-5 minutes, such as 3 minutes.

The processing unit may be configured to control the drive module to move the plunger rod to the mix plunger rod position and/or the second plunger rod position and/or to the injection plunger rod position based on the one or more elapsed time, such as delay times. For example, the processing unit may be configured to control the drive module to move the plunger rod to the second plunger rod position only after the reconstitution time has elapsed since completion of the movement of the plunger rod to the mix plunger rod position.

The reconstitution time may be based on a cartridge specification, e.g. the reconstitution time may be based on the cartridge code feature, e.g. the reconstitution time may be based on the code signal. The processing unit may be configured to determine the reconstitution time based on the code signal.

Alternatively or additionally, the reconstitution time may be based on a temperature, e.g. the reconstitution time may be based on the temperature of the medicament, e.g. the reconstitution time may be based on the temperature signal. For example, the reconstitution time may be longer for lower temperatures than for higher temperatures. The processing unit may be configured to determine the reconstitution time based on the temperature signal.

Alternatively or additionally, the reconstitution time may be based on the orientation signal. The processing unit may be configured to determine the reconstitution time based on the orientation signal.

Alternatively or additionally, the reconstitution time may be based on the first movement parameter. The processing unit may be configured to determine the reconstitution time based on the first movement parameter.

Alternatively or additionally, the reconstitution time may be based on resistance against movement of the plunger rod, such as on the resistance signal. The processing unit may be configured to determine the reconstitution time based on the resistance signal.

The processing unit may be configured to determine the reconstitution time based on the code signal and/or the temperature signal and/or the orientation signal and/or the first movement parameter and/or the resistance signal.

The plunger rod may be moved towards the retracted plunger rod position, such as to the retracted plunger rod position, following completion of the movement of the plunger rod to the injection plunger rod position. The processing unit may be configured to control the drive module to move the plunger rod towards the retracted plunger rod position following completion of the movement of the plunger rod to the injection plunger rod position.

Movement of the plunger rod towards the retracted plunger rod position, such as to the retracted plunger rod position, such as after completion of the movement of the plunger rod to the injection plunger rod position, may require that a dwell time has elapsed, e.g. since completion of the movement of the plunger rod to the injection plunger rod position. The dwell time may be chosen to allow sufficient time to ensure that the medicament is distributed into the tissue. The dwell time may be influenced by the medicament and/or concentration of the medicament and/or the amount of medicament and/or the temperature of the medicament. The dwell time may be based on a cartridge specification, e.g. the dwell time may be based on the cartridge code feature, e.g. the dwell time may be based on the code signal. The dwell time may be based on the temperature of the medicament, e.g. the dwell time may be based on the temperature signal.

The processing unit may be configured to control the drive module to move the plunger rod towards the retracted plunger rod position only after the dwell time has elapsed since completion of the movement of the plunger rod to the injection plunger rod position.

The dwell time may be based on a cartridge specification, e.g. the dwell time may be based on the cartridge code feature, e.g. the dwell time may be based on the code signal. The processing unit may be configured to determine the dwell time based on the code signal.

Alternatively or additionally, the dwell time may be based on a temperature, e.g. the dwell time may be based on the temperature of the medicament, e.g. the dwell time may be based on the temperature signal. For example, the dwell time may be longer for lower temperatures than for higher temperatures. The processing unit may be configured to determine the dwell time based on the temperature signal.

Alternatively or additionally, the dwell time may be based on the orientation signal. The processing unit may be configured to determine the dwell time based on the orientation signal.

Alternatively or additionally, the dwell time may be based on the first movement parameter. The processing unit may be configured to determine the dwell time based on the first movement parameter.

Alternatively or additionally, the dwell time may be based on resistance against movement of the plunger rod, such as on the resistance signal. The processing unit may be configured to determine the dwell time based on the resistance signal.

The processing unit may be configured to determine the dwell time based on the code signal and/or the temperature signal and/or the orientation signal and/or the first movement parameter and/or the resistance signal.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
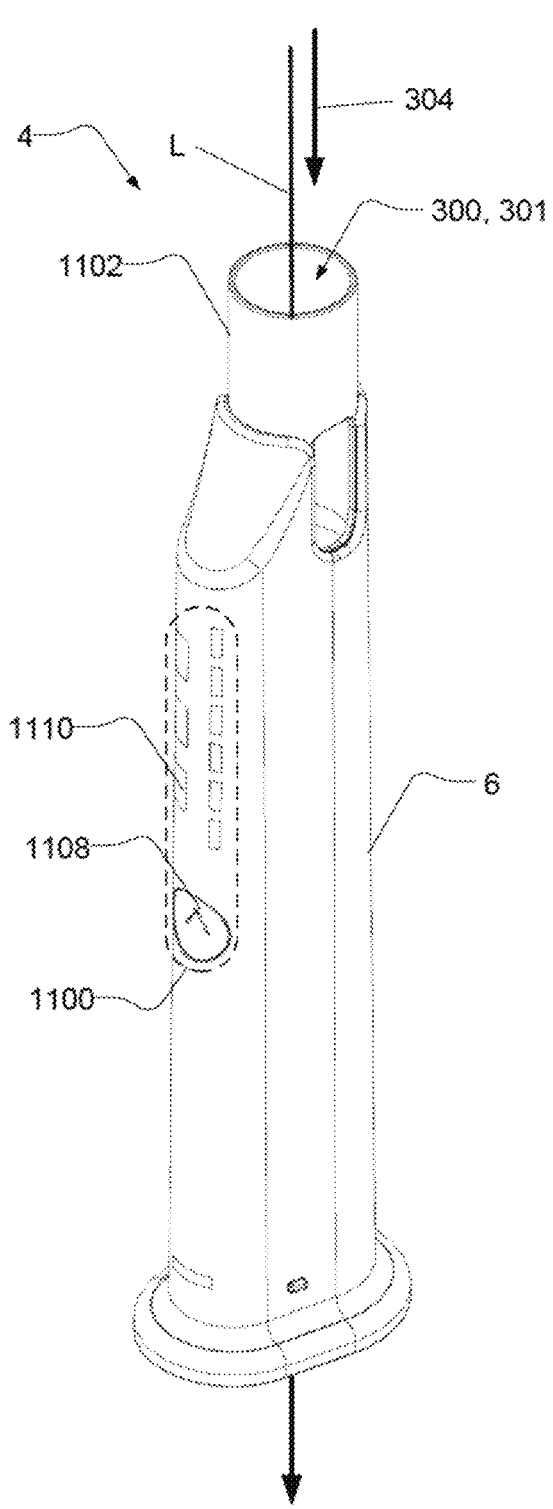
FIG. 1 illustrates an exemplary auto injector.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates an exemplary auto injector 4. The auto injector 4 may be configured for administering a medicament. The auto injector 4 may be an electronic auto injector.

The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis L.

The auto injector 4 may comprise a user interface 1100, as illustrated. The auto injector 4 comprises a trigger member, such as the contact member 1102. The contact member 1102 may be configured to be pressed against an injection site. The contact member 1102 may be movable in the cartridge receiving direction 304, relative to the housing, if pressed against the injection site. The contact member 1102 may be part of the user interface 1100.

The user interface 1100 may comprise a first input member 1108 as illustrated, e.g. a button. The first input member 1108 may provide for a user input from a user. For example, the first input member 1108 may be used for receiving a push from a user to proceed to a next step.

The user interface 1100 may comprise a first output member 1110 as illustrated, e.g. a plurality of LEDs. The first output member 1110 may provide for a user output to a user. The user interface 1100 may comprise a second output member (not shown), e.g. a speaker. The second output member may be configured to provide audible output to the user. For example, the first output member 1110 and/or the second output member may be used to indicate a step in the procedure to the user and/or to indicate an error message.

Figure 2:
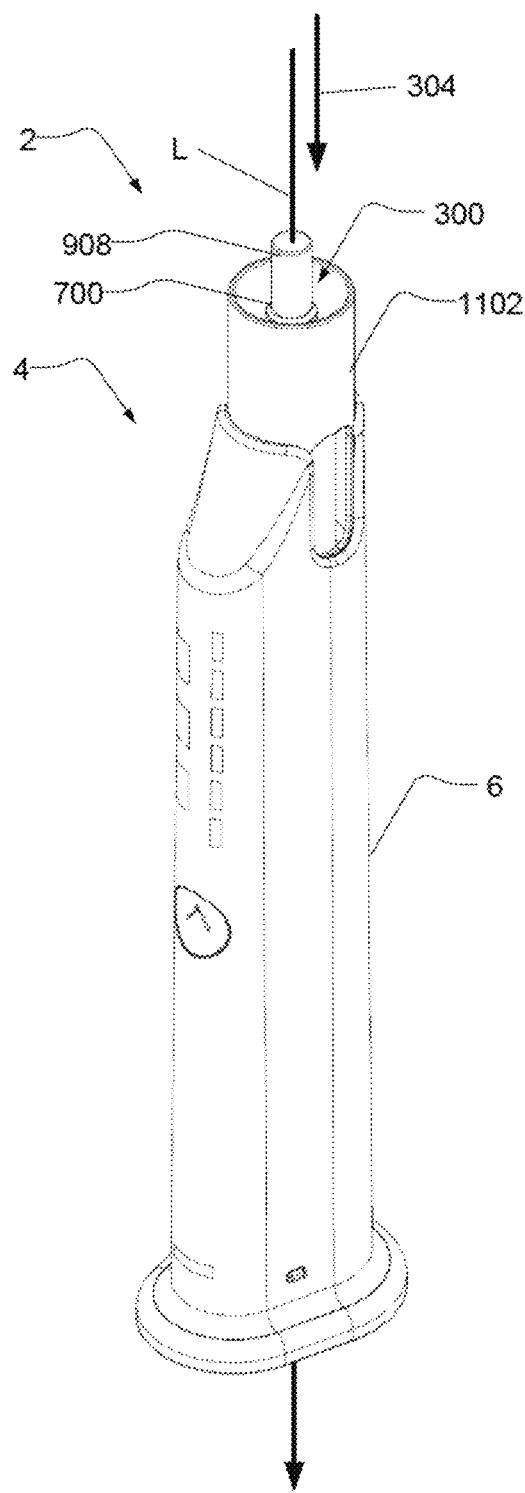
FIG. 2 illustrates an exemplary auto injector with a cartridge.

FIG. 2 illustrates an exemplary system 2. The system 2 comprises an auto injector 4, as described in relation to FIG. 1, and an exemplary cartridge 700 received in the cartridge receiver 300. The cartridge 700 is shown with a needle cover 908. The needle cover 908 extending out of the contact member 1102 to allow removal of the needle cover 908 from the cartridge 700.

Figure 3:
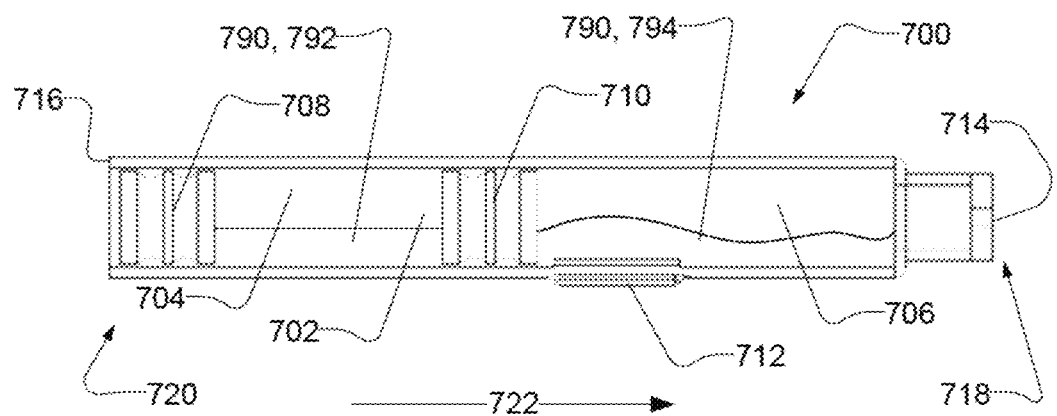
FIG. 3 schematically illustrates an exemplary cartridge.

FIG. 3 schematically illustrates an exemplary cartridge 700, such as a cartridge 700 being configured to be received in the cartridge receiver of an auto injector, such as the auto injector described in relation to previous figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at the first cartridge end 718. The cartridge may be configured to expel medicament through the cartridge outlet 714.

The cartridge comprises a first stopper 708 movable inside the cartridge compartment, e.g. in a first stopper direction 722, e.g. towards the first cartridge end. For example, the medicament may be expelled through the cartridge outlet 714 upon movement of the first stopper 708 in the first stopper direction. The cartridge comprises a cartridge back face 716 at the second cartridge end. The cartridge back face 716 comprises a cartridge back end opening for providing access to the first stopper 708 for a plunger rod.

As illustrated, the cartridge 700 may be a dual chamber cartridge. The cartridge comprises a second stopper 710 movable inside the cartridge compartment 702, e.g. in the first stopper direction 722, e.g. towards the first cartridge end. The cartridge compartment 702 comprises a first cartridge subcompartment 704 and a second cartridge subcompartment 706. The first cartridge subcompartment 704 is between the first stopper 708 and the second stopper 710. The second cartridge subcompartment 706 is between the second stopper 710 and the cartridge outlet 714. The cartridge comprises a bypass section 712 for providing fluid communication between the first cartridge subcompartment and the second cartridge subcompartment. The bypass section 712 provides fluid communication between the first cartridge subcompartment and the second cartridge subcompartment when the second stopper 710 is positioned in the bypass section 712.

The first cartridge subcompartment 704 contains a first medicament component 792 of the medicament 790. The first medicament component 792 may be a liquid as illustrated. The second cartridge subcompartment 706 contains a second medicament component 794 of the medicament 790. The second medicament component 794 may be a powder composition. By positioning of the second stopper 710 within the bypass section 712, the first medicament component 792 may be transmitted into the second cartridge subcompartment 706 via the bypass section 712, thereby mixing the first medicament component 792 and the second medicament component 794 to achieve the combined medicament 790.

FIGS. 4a-d schematically illustrates an exemplary cartridge assembly 600. The cartridge assembly 600 comprises an exemplary cartridge 700 and an exemplary cartridge code feature 1000. The cartridge 700 has a first cartridge end 718 and a second cartridge end 720. The first stopper direction 722 is from the second cartridge end 720 to the first cartridge end 718. The cartridge code feature 1000 is positioned near the second cartridge end 720, e.g. closer to the second cartridge end 720 than the first cartridge end 718. In another exemplary cartridge assembly, the cartridge code feature 1000 may be positioned near the first cartridge end 720.

FIGS. 4a-d illustrates different types of exemplary cartridge code features 1000.

FIG. 4a illustrates an exemplary cartridge assembly 600, wherein the cartridge code feature 1000 comprises two strips. The two strips may be coloured, e.g. differently coloured. The combination and/or sequence of colours may be indicative of a code of the cartridge code feature 1000.

FIG. 4b illustrates an exemplary cartridge assembly 600, wherein the cartridge code feature 1000 comprises bar codes. The cartridge code feature 1000 may comprise one or more bar codes. The bar code may be indicative of a number indicative of a code of the cartridge code feature 1000.

FIG. 4c illustrates an exemplary cartridge assembly 600, wherein the cartridge code feature 1000 comprises differently grated strips. For example, as illustrated, the cartridge code feature 1000 may comprise two strips wherein the first strip is grated at 45 deg., and the second strip is grated at −45 deg. The grating, and/or the grating of the strips relative to each other, may be indicative of a code of the cartridge code feature 1000.

FIG. 4d illustrates an exemplary cartridge assembly 600, wherein the cartridge code feature 1000 comprises an electromagnetically readable tag, such as an RFID tag or an NFC tag. The electromagnetically readable tag may contain data that is indicative of a code of the cartridge code feature 1000.

Figure 5:
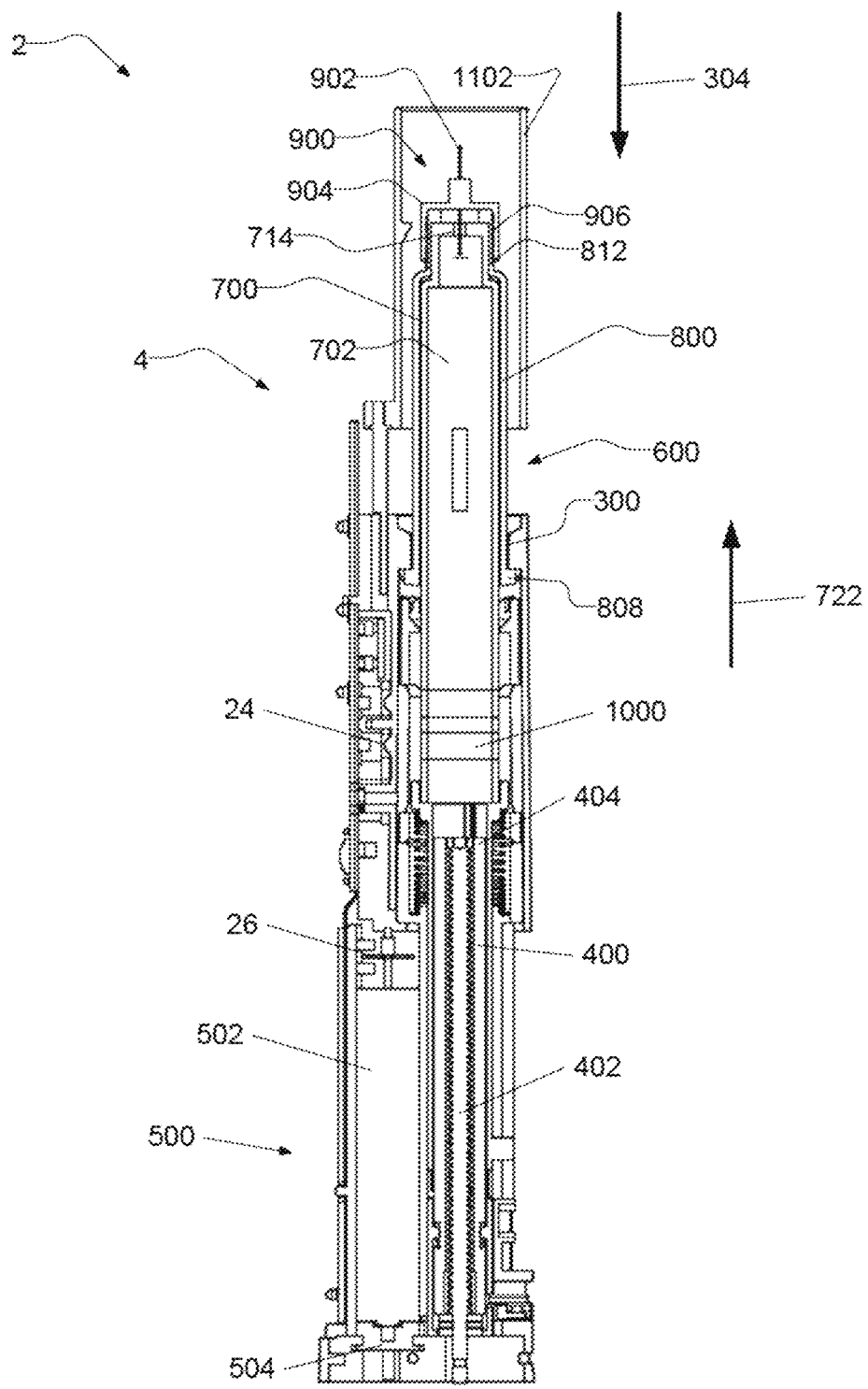
FIG. 5 schematically illustrates an exemplary auto injector with a cartridge assembly.

FIG. 5 illustrates an exemplary system 2. The system 2 comprises an auto injector 4, as described, for example, in relation to FIG. 1, and an exemplary cartridge assembly 600. The cartridge assembly 600 comprises a cartridge 700 with a cartridge compartment 702, a needle assembly 900, and a cartridge code feature 1000. The cartridge assembly 600 is received in the auto injector 4.

The cartridge assembly 600 comprises a cartridge holder 800. The cartridge holder 800 is configured for retention of the cartridge 700 in the cartridge receiver 300 of the auto injector 4. The cartridge holder 800 comprises a cartridge retention member 808. The cartridge retention member 808 engages with the cartridge receiver 300 for reception and retention of the cartridge 700 and the cartridge assembly 600 in the cartridge receiver 300.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800.

The needle 902 extends through the cartridge outlet 714 of the cartridge 700. The cartridge outlet 714 may be blocked by a resilient sealing being penetrated by the needle 902, when the needle assembly 900 is attached to the cartridge 700.

The auto injector 4 comprises a code sensor 24 configured to read the cartridge code feature 1000. When the cartridge assembly 600 is inserted, as shown, the cartridge code feature 1000 is lined up with the code sensor 24.

The auto injector 4 comprises a plunger rod 400. The plunger rod 400 is configured to advance a first stopper of the cartridge 700. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper of the cartridge 700, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400.

Although the example shown comprises a motor 502, which may be an electro-mechanical motor, it will be readily understood that the auto injector 4 may be realised having an alternative drive module, such as comprising a solenoid motor, a shape memory metal engine, an arrangement of springs and/or a pressurized gas configured to actuate the plunger rod 400.

The auto injector 4 comprises an ejection sensor 26, such as a plunger rod position sensor. The ejection sensor 26 is configured to detect the position of the plunger rod 400. In the illustrated example, the ejection sensor 26 comprises a tachometer configured to count/detect the revolutions of the motor 502. Thus, the position of the plunger rod 400 may be determined based on the count of revolutions of the motor 502. The ejection sensor 26 may, based on the detection of the position of the plunger rod 400, detect the expelling of medicament and/or air in the cartridge compartment. The position of the plunger rod 400 may be indicative of the position of the first stopper of the cartridge 700, e.g. the most advanced position of the plunger rod 400, e.g. while the cartridge 700 is in the cartridge receiver 300, may be indicative of the position of the first stopper of the cartridge 700.

FIGS. 6*a-d* schematically illustrate an auto injector 4 and a cartridge assembly 600. FIGS. 6*a-d* schematically illustrates exemplary positions of a contact member 1102 of the auto injector 4 in various situations.

The auto injector 4 comprises a cartridge receiver 300 configured for receiving and retaining a cartridge. The auto injector 4 comprises a contact member 1102. The contact member 1102 may be movable between an extended contact member position and a retracted contact member position. The contact member 1102 comprises a contact member protruding part 1112. The contact member protruding part 1112 is configured to move with the contact member 1102. The contact member 1102 may be biased, e.g. by a contact member spring (not shown), towards the extended contact member position.

The contact member comprises a needle cover engagement member 1114. The needle cover engagement member 1114 is configured to abut a needle cover abutment face, e.g. of a needle cover positioned on the cartridge inserted into the cartridge receiver 300.

The auto injector 4 comprises a contact member sensor 1104 configured to detect a position of the contact member 1102. The contact member sensor 1104 comprises a first contact member sensor 1130 and a second contact member sensor 1132. The first contact member sensor 1130 and the second contact member sensor 1132 may be optical sensors. The contact member sensor 1104 detects the position of the contact member 1102 by the contact member protruding part 1112 covering the first contact member sensor 1132 when the contact member 1102 is in a first contact member position, and the contact member protruding part 1112 covering the second contact member sensor 1132 when the contact member 1102 is in a second contact member position.

The first contact member position may be detected by the first contact member sensor 1130 being covered and the second contact member sensor 1132 being covered. The second contact member position may be detected by the first contact member sensor 1130 not being covered and the second contact member sensor 1132 being covered. The extended contact member position may be detected by the first contact member sensor 1130 not being covered and the second contact member sensor 1132 not being covered.

FIG. 6*a* schematically illustrates the auto injector 4 with no received cartridge and/or cartridge assembly. The contact member 1102 is in the extended contact member position. A cartridge may be inserted into the cartridge receiver 300 in the cartridge receiving direction 322 through the contact member 1102 defining a cartridge receiver opening 301.

FIG. 6*b* schematically illustrates the auto injector 4 with a cartridge assembly 600 received. The cartridge assembly 600 comprises a cartridge 700, a cartridge holder 800 and a needle assembly 900. The needle assembly comprises a needle 902 and a needle cover 908. The needle cover has a needle cover abutment face 910. The needle cover abutment face 910 engages the needle cover engagement member 1114 of the contact member 1102. The contact member 1102 is in the second contact member position, e.g. caused by the presence of the needle cover 908 and the abutment of the needle cover abutment face 910 on the needle cover engagement member 1114. The contact member protruding part 1112 covers the second contact member sensor 1132. The contact member protruding part 1112 does not cover the first contact member sensor 1130.

FIG. 6*c* schematically illustrates the auto injector 4 with a cartridge assembly 600 received. Compared to FIG. 6*b*, the needle cover 908 has been removed. The contact member 1102 is in the extended contact member position. The contact member 1102 is allowed to be moved to the extended contact member position since the needle cover abutment face 910 does not abut the needle cover engagement member 1114. The contact member protruding part 1112 has moved with the contact member 1102. The contact member protruding part 1112 does not cover the second contact member sensor 1132. The contact member protruding part 1112 does not cover the first contact member sensor 1130.

FIG. 6*d* schematically illustrates the auto injector 4 with a cartridge assembly 600 received. The contact member 1102 is in the first contact member position. The first contact member position may be the retracted contact member position, or close to the retracted contact member position. The contact member 1102 may have been moved to the first contact member position by the contact member 1102 being pressed against an injection site, thereby inserting the needle 902 into the injection site. The contact member protruding part 1112 has moved with the contact member 1102. The contact member protruding part 1112 covers the first contact member sensor 1130. The contact member protruding part 1112 covers the second contact member sensor 1132.

Figure 7:
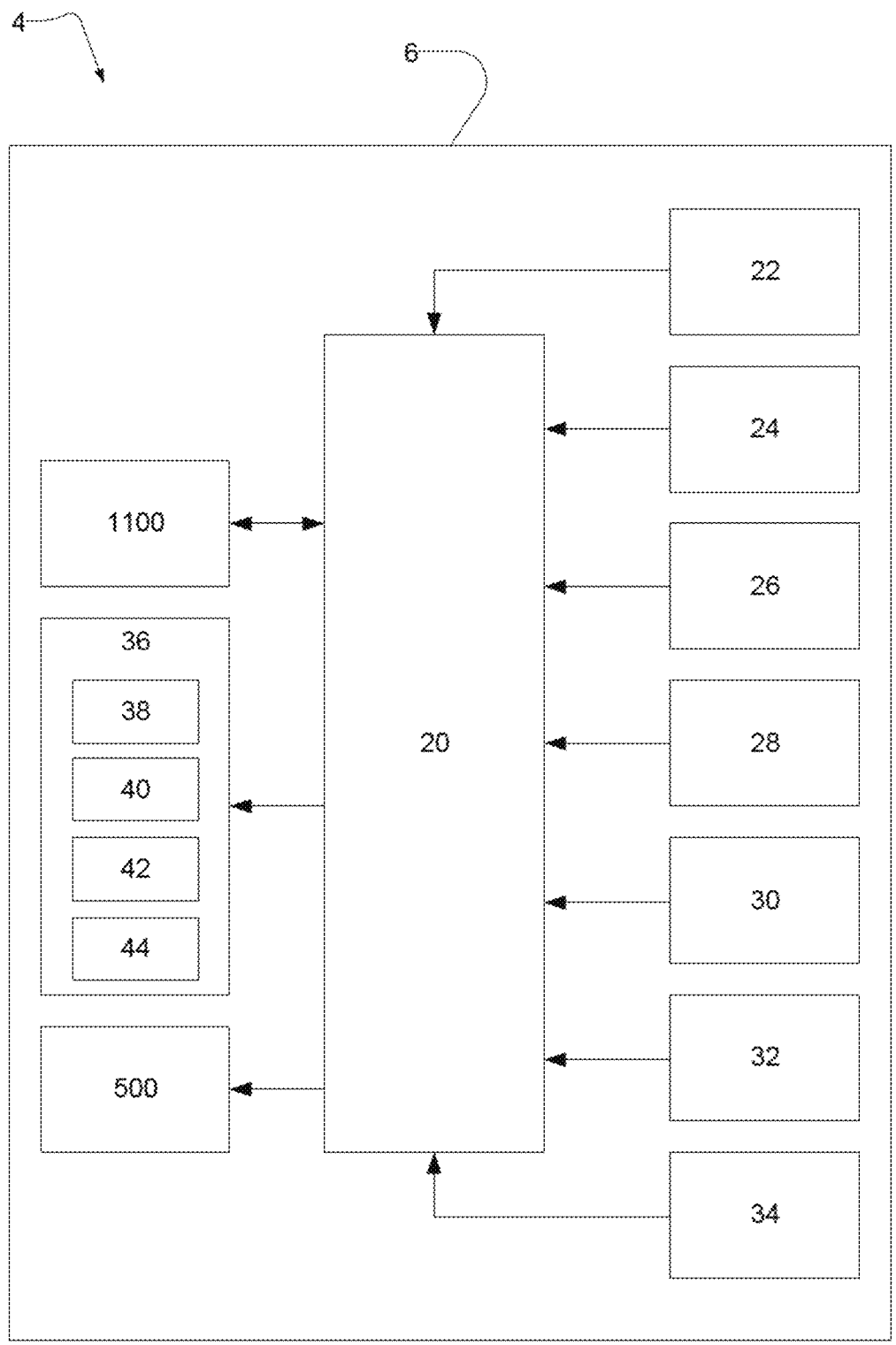
FIG. 7 shows a block diagram of an exemplary auto injector.

FIG. 7 shows a block diagram of an exemplary auto injector 4. The auto injector 4 comprises a plurality of sensors 22, 24, 26, 28, 30, 32, 34, a processing unit 20, a drive module 500, a user interface 1100, and a temperature control unit 36. The sensors 22, 24, 26, 28, 30, 32, 34 are coupled to the processing unit 20. The user interface 1100 is coupled to the processing unit 20. The processing unit is coupled to the drive module 500.

The processing unit 20 receives signals from the sensors 22, 24, 26, 28, 30, 32, 34 and the user interface 1100. The processing unit 20 is configured to control the drive module 500. The processing unit 20 may control the drive module 500 based on one or more of the received signals from the sensors 22, 24, 26, 28, 30, 32, 34 and the user interface 1100. The processing unit 20 is configured to provide user outputs via the user interface 1100. The processing unit 20 is configured to control the temperature control unit 36. The processing unit 20 may control temperature control unit 36 based on one or more of the received signals from the sensors 22, 24, 26, 28, 30, 32, 34 and the user interface 1100.

The auto injector 4 comprises an orientation sensor 22. The orientation sensor 22 is configured to provide an orientation signal indicative of the orientation of a cartridge received in the auto injector 4. For example, the orientation sensor 22 may be configured to detect the orientation of the auto injector 4. The orientation of the cartridge may be determined based on the orientation of the auto injector 4. The orientation sensor 22 may be configured to detect the direction of gravity. For example, the orientation sensor 22 may comprise an accelerometer.

The processing unit 20 is coupled to the orientation sensor 22. The processing unit 20 is configured to receive the orientation signal. The processing unit 20 may determine the orientation of the cartridge based on the orientation signal. The processing unit 20 may control the drive module 500 based on the orientation signal. For example, the processing unit 20 may be configured to control the drive module 500 to move the plunger rod based on the orientation signal. For example, the processing unit 20 may be configured to control the drive module 500 to move the plunger rod towards the extended plunger rod position, such as to a pre-mix plunger rod position and/or a mix plunger rod position and/or the prime plunger rod position, only if the cartridge outlet is pointing upwards. Alternatively or additionally, the processing unit 20 may provide user output via the user interface 1100 based on the orientation signal.

The auto injector 4 comprises a code sensor 24. The code sensor 24 is configured to read a cartridge code feature, and provide a code signal indicative of a cartridge code feature. For example, the code sensor may be configured to read/detect a colour code.

The processing unit 20 is coupled to the code sensor 24. The processing unit 20 is configured to receive the code signal. The processing unit 20 may determine the cartridge code feature of the cartridge assembly based on the code signal. The processing unit 20 may control the drive module 500 based on the code signal. For example, the processing unit 20 may be configured to control the drive module 500 to move the plunger rod towards the extended plunger rod position, such as to the pre-mix plunger rod position and/or the mix plunger rod position and/or the prime plunger rod position and/or the injection plunger rod position, based on the code signal. The processing unit 20 may be configured to determine a threshold, such as a plunger rod threshold, and/or a resistance threshold, based on the code signal. Alternatively or additionally, the processing unit 20 may provide user output via the user interface 1100 based on the code signal.

The auto injector 4 comprises an ejection sensor 26, such as a plunger rod position sensor. The ejection sensor 26 is configured to detect the position of the plunger rod of the auto injector 4, and provide an ejection sensor signal indicative of the position of the plunger rod. The ejection sensor 26 may comprise a tachometer coupled to the drive module 500.

The processing unit 20 is coupled to the ejection sensor 26. The processing unit 20 is configured to receive the ejection sensor signal. The processing unit 20 may determine the position of the plunger rod based on the ejection sensor signal. The processing unit 20 may control the drive module 500 based on the ejection sensor signal. For example, the processing unit 20 may be configured to control the drive module 500 to start, stop or continue movement of the plunger rod based on the ejection sensor signal. For example, the processing unit 20 may be configured to determine a present plunger rod position based on the ejection sensor signal. The plunger rod being in the pre-mix plunger rod position and/or the mix plunger rod position and/or the prime plunger rod position and/or the injection plunger rod position may be determined based on the ejection sensor signal. Alternatively or additionally, the processing unit 20 may provide user output via the user interface 1100 based on the ejection sensor signal.

The auto injector 4 comprises a cartridge sensor 28. The cartridge sensor 28 is configured to detect reception of a cartridge assembly in the auto injector 4. The cartridge sensor 28 provides a cartridge sensor signal indicative of reception of a cartridge assembly.

The processing unit 20 is coupled to the cartridge sensor 28. The processing unit 20 is configured to receive the cartridge sensor signal. The processing unit 20 may control the drive module 500 based on the cartridge sensor signal. For example, the processing unit 20 may be configured to control the drive module 500 to start movement of the plunger rod if a cartridge assembly is received, and/or only if a cartridge assembly is received. Alternatively or additionally, the processing unit 20 may provide user output via the user interface 1100 based on the cartridge sensor signal.

The code sensor 24 and the cartridge sensor 28 may be the same sensor, e.g. the code sensor 24 may be configured to detect reception of a cartridge assembly and subsequently read the cartridge code feature.

The auto injector 4 comprises a needle sensor 30. The needle sensor 30 is configured to detect a needle, and/or a needle assembly, and/or a needle cover of a needle assembly, of the cartridge assembly, when the cartridge assembly is received in the auto injector 4. The needle sensor 30 provides a needle signal indicative of the presence of a needle, and/or a needle assembly, and/or a needle cover of a needle assembly, of the cartridge assembly.

The processing unit 20 is coupled to the needle sensor 30. The processing unit 20 is configured to receive the needle signal. The processing unit 20 may control the drive module 500 based on the needle signal. For example, the processing unit 20 may be configured to control the drive module 500 to start movement of the plunger rod, e.g. towards the extended plunger rod position, such as to the pre-mix plunger rod position and/or the mix plunger rod position and/or the prime plunger rod position and/or the injection plunger rod position, only if a needle is present, and/or only if a needle cover is not present, such as removed. Detection of a needle cover may be indicative of a needle being present. The processing unit 20 may be configured to control the drive module 500 to start only if a needle cover has been detected, and subsequently is not detected, e.g. it has been removed. Alternatively or additionally, the processing unit 20 may provide user output via the user interface 1100 based on the needle signal.

Figure 6:
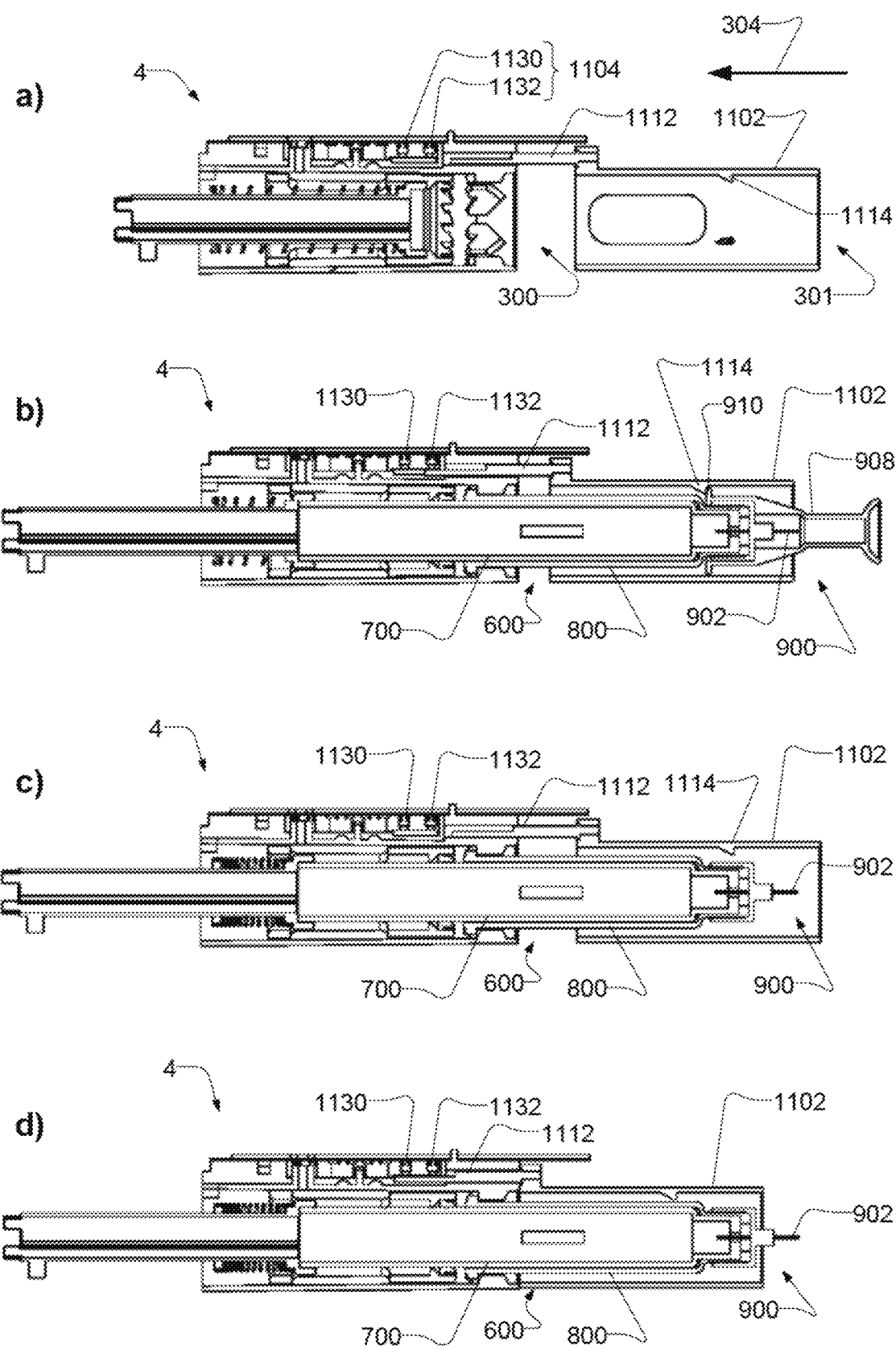
FIG. 6 *a-d* schematically illustrate an auto injector and a cartridge assembly.

The needle sensor 30 may be part of the contact member sensor, as exemplified in FIG. 6.

The auto injector 4 comprises a temperature sensor 32. The temperature sensor 32 is configured to detect a temperature, such as a temperature of the auto injector and/or of the cartridge and/or of the medicament. The temperature sensor 32 is configured to provide a temperature signal indicative of the temperature.

The processing unit 20 is coupled to the temperature sensor 32. The processing unit 20 is configured to receive the temperature signal. The processing unit 20 may be configured to determine the temperature, such as the temperature of the auto injector and/or of the cartridge and/or of the medicament based on the temperature signal. The processing unit 20 may control the drive module 500 based on the temperature signal. For example, the processing unit 20 may be configured to control the drive module 500 to move the plunger rod towards the extended plunger rod position, such as to the pre-mix plunger rod position and/or the mix plunger rod position and/or the prime plunger rod position and/or the injection plunger rod position, based on the temperature signal. The processing unit 20 may determine plunger rod positions based on the temperature signal. For example, the processing unit 20 may be configured to determine the pre-mix plunger rod position and/or the mix plunger rod position and/or the prime plunger rod position and/or the injection plunger rod position based on the temperature signal. Alternatively or additionally, the processing unit 20 may provide user output via the user interface 1100 based on the temperature signal.

The auto injector 4 comprises a resistance sensor 34. The resistance sensor 34 is configured to detect resistance against movement of the plunger rod of the auto injector 4. The resistance sensor 34 may be configured to detect resistance against movement of the plunger rod based on measurements of the drive module 500. For example, the resistance sensor 34 may be configured to detect the electrical current of a motor of the drive module 500. The resistance sensor 34 is configured to provide a resistance signal indicative of resistance against movement of the plunger rod.

The processing unit 20 is coupled to the resistance sensor 34. The processing unit 20 is configured to receive the resistance signal. The processing unit 20 may be configured to determine the resistance against movement of the plunger rod based on the resistance signal. The processing unit 20 may control the drive module 500 based on the resistance signal. For example, the processing unit 20 may be configured to control the drive module 500 to adjust movement of the plunger rod based on the resistance signal. For example, the processing unit 20 may be configured to control the drive module 500 to start, stop or continue movement of the plunger rod based on the resistance signal. Alternatively or additionally, the processing unit 20 may provide user output via the user interface 1100 based on the resistance signal.

The auto injector 4 comprises a temperature control unit 36. The temperature control unit 36 is configured to detect configured to alter the temperature, such as a temperature of the auto injector and/or of the cartridge and/or of the medicament, e.g. based on the temperature of the auto injector and/or of the cartridge and/or of the medicament, such as on the temperature signal. For example, the temperature control unit 36 is configured to alter the temperature of the cartridge when received in the cartridge receiver.

The processing unit 20 is coupled to the temperature control unit 36. The processing unit 20 is configured to control the temperature control unit 36. The processing unit 20 may be configured to alter the temperature, such as the temperature of the auto injector and/or of the cartridge and/or of the medicament, e.g. based on the temperature signal. For example, the processing unit 20 may be configured to control the temperature control unit 36 to raise the temperature of the auto injector and/or of the cartridge and/or of the medicament, based on the temperature signal.

The temperature control unit 36 may comprise a heating element 38. The heating element 38 may be configured to raise the temperature of the auto injector and/or of the cartridge and/or of the medicament. The heating element 38 may be a resistive heating element. The heating element 38 may be a dielectric heating element.

The temperature control unit 36 may comprise a cooling element 40. The cooling element 40 may be configured to lower the temperature of the auto injector and/or of the cartridge and/or of the medicament.

The temperature control unit 36 may comprise a contact element 42. The contact element 42 may be configured to be in contact with the cartridge when received in the cartridge receiver. The contact element 42 may provide an increased heat transfer between the temperature control unit 36 and the auto injector and/or the cartridge and/or the medicament.

The temperature control unit 36 may comprise a coil element 44. The coil element 44 may be configured to surround an entire perimeter of the cartridge when received in the cartridge receiver. The coil element 44 may provide an increased heat transfer between the temperature control unit 36 and the auto injector and/or the cartridge and/or the medicament.

The auto injector 4 is illustrated comprising all of the above mentioned elements. However, alternatively, the auto injector may comprise only one or any combination of one or more of the above mentioned elements.

The auto injector comprises a user interface 1100. The user interface 1100 may comprise one or more input members, e.g. a first input member, for receiving a user input. The user interface is configured to provide a user input signal indicative of the received user input. The user interface 1100 may provide a first input signal and/or a second input signal.

The processing unit 20 is coupled to the user interface 1100. The processing unit 20 is configured to receive the user input signal, such as the first input signal and/or the second input signal. The processing unit 20 may control the drive module 500 based on the user input signal. For example, the processing unit 20 may be configured to control the drive module 500 to move the plunger rod towards the extended plunger rod position, such as to the pre-mix plunger rod position and/or the mix plunger rod position and/or the prime plunger rod position and/or the injection plunger rod, based on the user input signal and/or following the user input signal.

The auto injector comprises a housing 6 accommodating the sensors 22, 24, 26, 28, 30, 32, 34, processing unit 20, user interface 1100, drive module 500, and temperature control unit 36.

FIGS. 8*a-f* schematically illustrate exemplary cartridge assemblies 600 and a plunger rod 400. The cartridge assembly 600 comprises a cartridge 700, such as the cartridge described in relation to FIG. 3, a cartridge holder 800, and a needle assembly 900. For intelligibility, the auto injector comprising the plunger rod 400 is not shown.

The cartridge holder 800 comprises a cartridge retention member 808. The cartridge retention member 808 is configured for engagement with a cartridge receiver of the auto injector. The cartridge holder 800 comprises a needle assembly coupling portion 812. The needle assembly coupling portion 812 is configured for engagement with a cartridge holder coupling portion 906 of the needle assembly 900. The needle assembly coupling portion 812 allows attachment of a needle to the cartridge 700.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700.

FIG. 8a schematically illustrates a situation wherein the plunger rod 400 is in an exemplary retracted plunger rod position. The cartridge 700 may be a new cartridge. The first stopper 708 is positioned in an initial position. The second stopper 710 is in an initial position, e.g. behind the bypass section 712, wherein the bypass section 712 does not form a fluid connection between the first subcompartment 704 and the second subcompartment 706.

FIG. 8b schematically illustrates a situation wherein the plunger rod 400 is in an exemplary pre-mix plunger rod position. Compared to FIG. 8a, the plunger rod 400 is moved towards an extended plunger rod position. A plunger rod front end 410 of the plunger rod 400 abuts the first stopper 708. Thus, the plunger rod 400 has started to move the first stopper 708 in the first stopper direction 722, by movement in the first plunger rod direction 422. The second stopper 710 is in a position, e.g. behind the bypass section 712, wherein the bypass section 712 does not form a fluid connection between the first subcompartment 704 and the second subcompartment 706.

FIG. 8c schematically illustrates a situation wherein the plunger rod 400 is in an exemplary position wherein a fluid connection is established between the first subcompartment 704 and the second subcompartment 706 via the bypass section 712. The plunger rod front end 410 of the plunger rod 400 abuts the first stopper 708. The plunger rod 400 has moved the first stopper 708 in the first stopper direction 722, by movement in the first plunger rod direction 422. The second stopper 710 is in the bypass section 712, wherein the bypass section 712 forms a fluid connection between the first subcompartment 704 and the second subcompartment 706. Thus, further movement of the first stopper 708 in the first stopper direction 722, e.g. by movement of the plunger rod 400 in the first plunger rod direction 422, will transmit the content of the first subcompartment 704, e.g. a first medicament component (not shown) into the second subcompartment 706, e.g. through the bypass section 712.

FIG. 8d schematically illustrates a situation wherein the plunger rod 400 is in an exemplary mix plunger rod position. The plunger rod front end 410 abuts the first stopper 708. The first stopper 708 abuts the second stopper 710. The first subcompartment 704 is compressed. The second stopper 710 is in a position after the bypass section 712. Thus, the fluid connection between the first subcompartment 704 and the second subcompartment 706 has been closed.

FIG. 8e schematically illustrates a situation wherein the plunger rod 400 is in an exemplary prime plunger rod position. Compared to FIG. 8d, the plunger rod 400 is moved towards an extended plunger rod position, e.g. to expel air from the cartridge compartment 702.

FIG. 8f schematically illustrates a situation wherein the plunger rod 400 is in an exemplary injection plunger rod position. For example after complete injection, the plunger rod 400 may be in the injection plunger rod position. The first stopper 708 and the second stopper 710 is in a position close to the cartridge outlet 714. Contents of the cartridge component, e.g. the medicament, has been expelled, e.g. through the cartridge outlet 714 and/or the needle 902. A residual volume of the medicament may be remaining in the cartridge.

Figure 9:
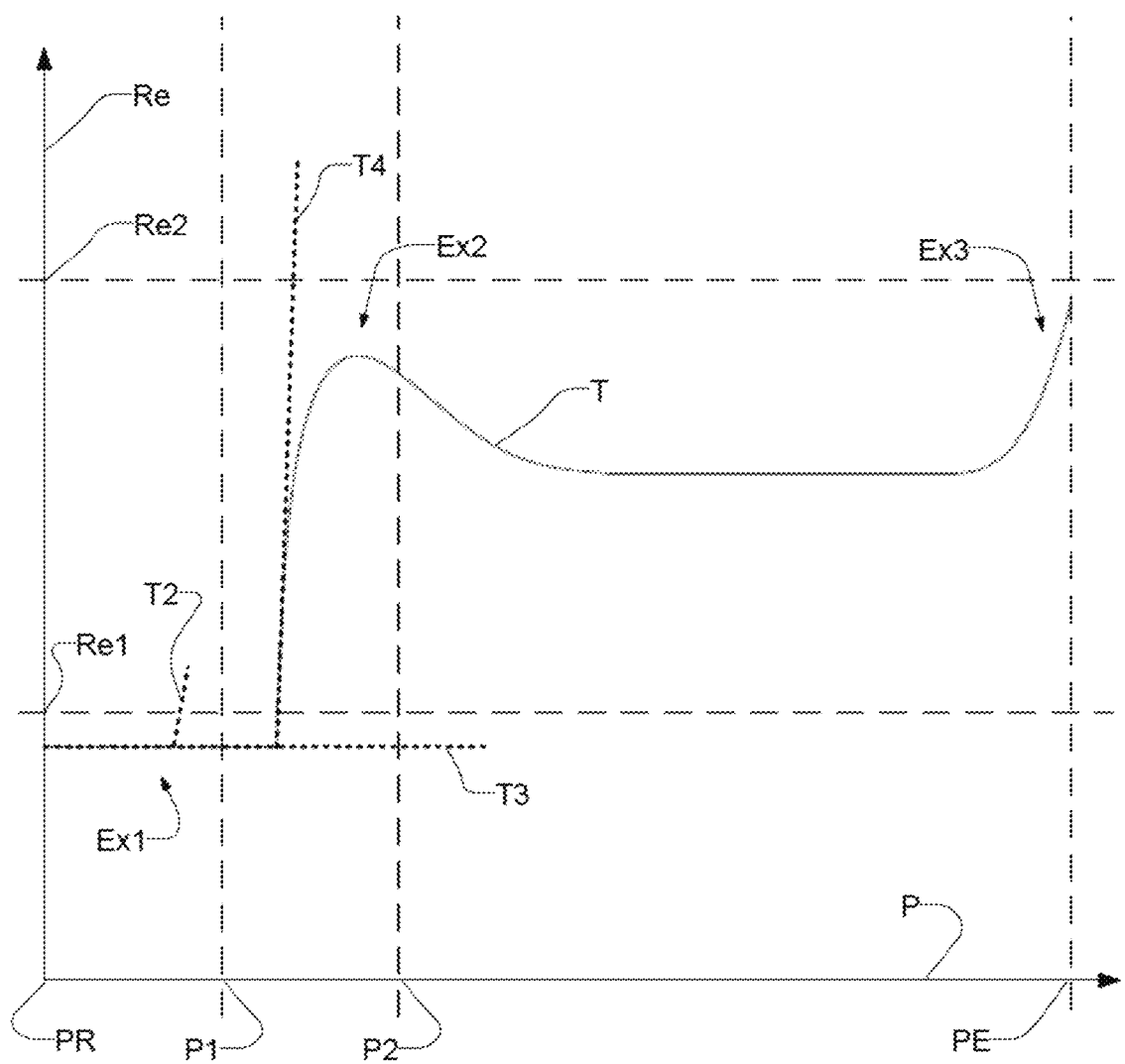
FIG. 9 shows an exemplary graph of resistance vs. position.

FIG. 9 shows an exemplary trace T of resistance Re against movement of the plunger rod dependent on the position P of the plunger rod. The plunger rod is moved from a retracted plunger rod position PR to an extended plunger rod position PE. In the beginning of the movement, the resistance against movement of the plunger rod is constant Ex1, e.g. the plunger rod does not yet push a stopper. Afterwards, a plunger rod front end of the plunger rod abuts a first stopper of the cartridge, and the resistance against movement of the plunger rod increases Ex2. The increased resistance is caused by the resistance against movement of the first stopper, e.g. due to frictional force. The resistance may decrease slightly after the first stopper has started moving, as illustrated. When the plunger rod approaches the extended plunger rod position PE, the resistance may increase again Ex3, e.g. due to the first stopper approaching an end of the cartridge.

The trace T is an example of resistance against plunger rod movement when the cartridge received is a new and/or unused and/or normal cartridge. Determining a cartridge parameter may be based on the resistance and/or plunger rod position. Determining the cartridge parameter may be based on one or more thresholds, such as resistance thresholds, such as a low resistance threshold Re1 and/or a high resistance threshold Re2, and/or plunger rod thresholds, such as a first plunger rod threshold P1 and/or a second plunger rod threshold P2.

Other situations, such as situations wherein the cartridge received is apparently used and/or flawed, are exemplified by additional exemplary traces, T2, T3, T4.

Trace T2 illustrates an exemplary situation wherein the resistance against movement increases above the low resistance threshold Re1 before the plunger rod position has reached the first plunger rod threshold P1. Such situation may for example indicate a flawed cartridge, or that something is blocking the plunger rod from moving. Following such situation, the plunger rod may be retracted to the retracted plunger rod position and an error message may be provided through a user interface.

Trace T3 illustrates an exemplary situation wherein the resistance against movement has not increased above the low resistance threshold Re1 before the plunger rod position has reached the second plunger rod threshold P2. Such situation may for example indicate a cartridge wherein the first stopper is in an advanced position, e.g. a used cartridge. Following such situation, the plunger rod may be retracted to the retracted plunger rod position and an error message may be provided through a user interface.

Trace T4 illustrates an exemplary situation wherein the resistance against movement increases above the high resistance threshold Re2, e.g. after the plunger rod position has passed the first plunger rod threshold P1. Such situation may for example indicate that the first stopper is blocked from moving, e.g. the cartridge may be flawed. Following such situation, the plunger rod may be retracted to the retracted plunger rod position and an error message may be provided through a user interface.

The thresholds, such as the low resistance threshold Re1, the high resistance threshold Re2, the first plunger rod threshold P1, and/or the second plunger rod threshold P2 may be individually determined for the cartridge received. For example, the processing unit of the auto injector may be configured to determine one or more of the thresholds, based on a cartridge code feature of the cartridge and/or cartridge assembly received.

Figure 10:
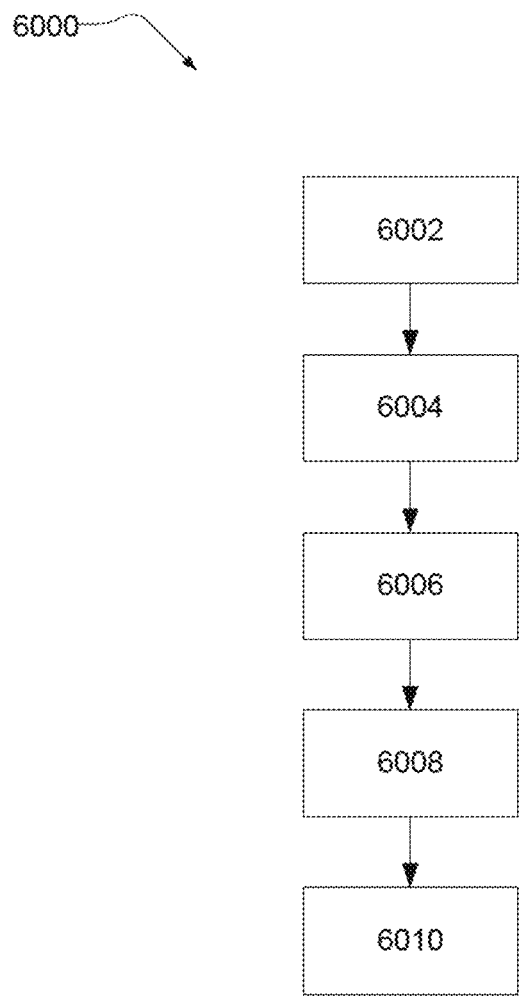
FIG. 10 shows a flow chart of an exemplary method.

FIG. 10 shows a flow chart of an exemplary method 6000 for operating an auto injector. The method 6000 comprises: receiving 6002 a temperature signal from a temperature sensor indicative of the temperature of the medicament; moving 6004 the plunger rod from a first plunger rod position to a mix plunger rod position with a mix plunger rod speed; moving 6006 the plunger rod from the mix plunger rod position to a second plunger rod position after a reconstitution time has elapsed since completion of movement of the plunger rod to the mix plunger rod position. The method 6000 may further comprise receiving 6008 a trigger event; and moving 6010 the plunger rod to an injection plunger rod position.

The auto injector may comprise a cartridge receiver configured to receive a cartridge comprising a first stopper and a cartridge compartment containing the medicament. The cartridge compartment may have a first cartridge subcompartment containing a first medicament component of the medicament and a second cartridge subcompartment containing a second medicament component of the medicament. The auto injector may further comprise a plunger rod configured to move the first stopper, and the temperature sensor.

The mix plunger rod position may be selected to position the first stopper in a position wherein the first medicament component is mixed with the second medicament component.

The movement 6004 from the first plunger rod position to the mix plunger rod position may be based on the temperature signal.

The second plunger rod position may be a prime plunger rod position. The prime plunger rod position may be selected to position the first stopper in a position wherein air in the cartridge compartment is reduced to an amount appropriate for injection.

Moving 6004 the plunger rod to the mix plunger rod position may follow detection of the cartridge being received in the cartridge receiver and/or reception of a first input signal. For example, moving 6004 the plunger rod to the mix plunger rod position may be performed only after a cartridge is detected and the first input signal is received.

Figure 12:
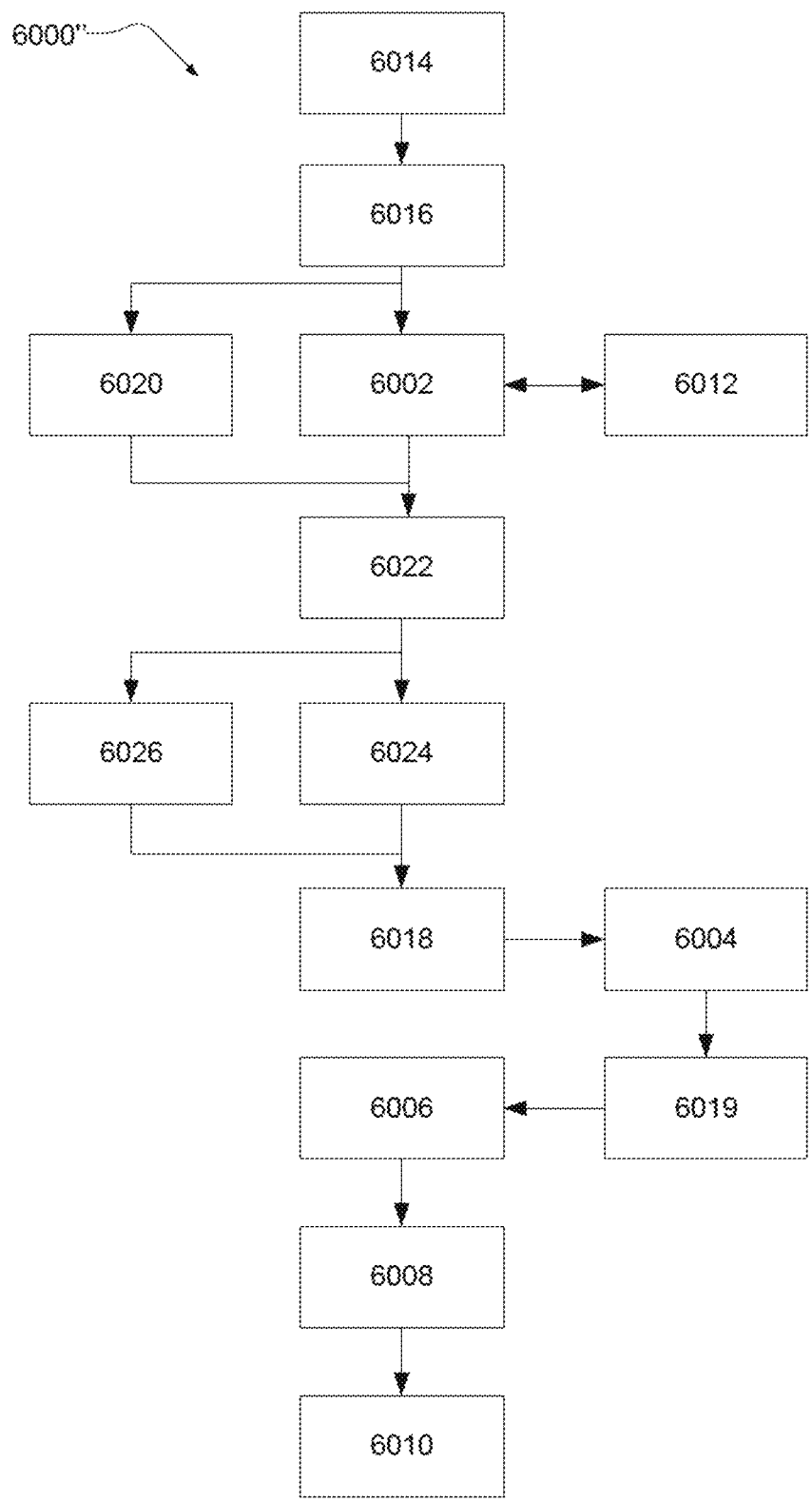
FIG. 12 shows a flow chart of an exemplary method.

Alternatively or additionally, moving 6004 the plunger rod to the mix plunger rod position may be preceded by determining orientation of the cartridge (as described in more detail in relation to FIG. 12). For example, moving 6004 the plunger rod to the mix plunger rod position may require that the outlet of the cartridge is pointing upwards, e.g. determined by determining orientation of the cartridge. Moving 6004 the plunger rod to the mix plunger rod position may be temporary paused if the orientation of the cartridge is not within a predefined range of orientations.

Moving 6006 the plunger rod to the second plunger rod position may require that the outlet of the cartridge is pointing upwards, e.g. determined by determining orientation of the cartridge. Moving 6006 the plunger rod to the second plunger rod position may be temporary paused if the orientation of the cartridge is not within a predefined range of orientations.

Moving 6006 the plunger rod from the mix plunger rod position to the second plunger rod position may require that a reconstitution time has elapsed since completion of movement of the plunger rod to the mix plunger rod position. The reconstitution time may be based on the temperature. Receiving 6002 the temperature signal may be performed additionally or alternatively after moving 6004 the plunger rod to the mix plunger rod position, such as to determine the reconstitution time.

Receiving 6008 the trigger event may comprise receiving a user input signal from a user interface, e.g. receiving the trigger event from a trigger member, e.g. originating from a user pressing a button. The trigger event may originate from a user indicating a start of injection. The trigger event may originate from a user pressing a front part of the auto injector against an intended injection site. The trigger event may comprise a contact member signal being indicative of a contact member of the auto injector being in a first contact member position.

Figure 11:
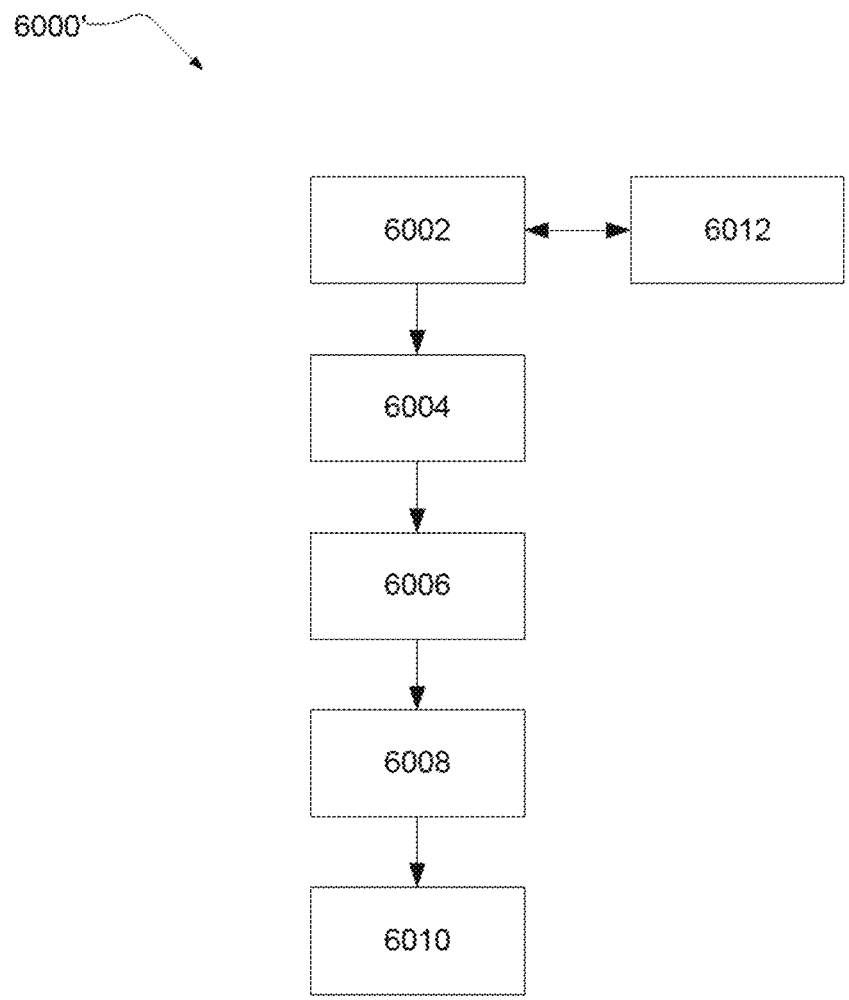
FIG. 11 shows a flow chart of an exemplary method.

Moving 6010 the plunger rod to the injection plunger rod position may result in ejection of the medicament through the cartridge outlet, such as through a needle. Moving 6010 the plunger rod may follow reception of the trigger event 6008, e.g. after completion of movement 6006 of the plunger rod to the second plunger rod position FIG. 11 shows a flow chart of an exemplary method 6000'. The method 6000' comprises the same steps of the method 6000 as explained in relation to the previous figure. However the method 6000' is an example of a method comprising an additional step of altering 6012 a temperature.

The method 6000' comprises altering 6012 the temperature of the auto injector and/or of the cartridge and/or of the medicament. The temperature may be altered following receiving 6002 the temperature signal indicative of the temperature of the medicament.

The temperature may be altered while receiving 6002 the temperature signal. For example, the temperature signal may be received 6002 indicating that the temperature is too low, the temperature may be raised by altering 6012 the temperature, afterwards the temperature signal may again be received 6002. This loop may continue until the temperature is within a predefined range. When the received 6002 temperature signal indicates that the temperature signal is within the predefined range, the method 6000' may continue to the next step of moving 6004 the plunger rod to the mix plunger rod position. The method 6000' may comprise altering 6012 the temperature concurrently with other steps of the method, e.g. while moving 6004 the plunger rod to the mix plunger rod position, e.g. to optimize subsequent steps of the method 6000'.

FIG. 12 shows a flow chart of an exemplary method 6000". The method 6000" comprises the same steps of the method 6000' as explained in relation to the previous figure. However the method 6000" is an example of a method comprising additional steps of receiving 6014 a first input signal; detecting 6016 reception of the cartridge, e.g. in the cartridge receiver of the auto injector; determining 6018 orientation of the cartridge; and reading 6020 a cartridge code feature; detecting 6022 needle cover removal; moving 6024 the plunger rod to the first plunger rod position, such as a pre-mix plunger rod position; and detecting 6026 resistance against movement of the plunger rod; and determining 6019 reconstitution time.

Receiving 6014 the first input signal may comprise receiving a user input signal from a user interface, e.g. originating from a user pressing a button. The first input signal may originate from a user turning on the auto injector.

Detecting 6016 reception of the cartridge may comprise detection of a user inserting the cartridge into the cartridge receiver through a cartridge receiver opening. Detecting 6016 reception of the cartridge may comprise detecting presence of a cartridge in the cartridge receiver.

Receiving 6014 the first input signal and detecting 6016 reception of the cartridge may be interchanged.

Determining 6018 orientation of the cartridge may comprise determining orientation by an orientation sensor, such as an accelerometer. Determining 6018 orientation of the cartridge may comprise determining orientation of the auto injector. Determining 6018 orientation of the cartridge may comprise determining whether an outlet of the cartridge is pointing upwards.

The method 6000" comprises reading 6020 a cartridge code feature. The cartridge code feature may be indicative of one or more cartridge specifications. The subsequent steps of the method 6000" may comprise adaptations based on the cartridge specifications. For example, subsequent steps of the method 6000" may be tailored to the specific cartridge received and identified.

Reading 6020 the cartridge code feature may be performed concurrently with receiving 6002 the temperature signal. However, alternatively, it may be performed sequentially. For example, reading 6020 the cartridge code feature may be performed prior to receiving 6002 the temperature signal, or reading 6020 the cartridge code feature may be performed after receiving 6002 the temperature signal Detecting 6022 needle cover removal may be a prerequisite of initiating movement of the plunger rod. For example, needle cover removal may be indicative of intended use of the cartridge received.

Moving 6024 the plunger rod to the first plunger rod position may comprise initial movement of a first stopper of the cartridge, e.g. movement of the first stopper without commencing mixing of a two-component medicament.

Moving 6024 the plunger rod to the first plunger rod position may follow detection 6016 of the cartridge being received in the cartridge receiver and reception 6014 of the first input signal. For example, moving 6024 the plunger rod to the first plunger rod position may be performed only after a cartridge is detected 6016 and the first input signal is received 6014.

Moving 6024 the plunger rod to the first plunger rod position may be performed concurrently with the steps of receiving 6002 the temperature signal, optionally altering 6012 the temperature, and reading 6020 the cartridge code feature.

Detecting 6026 resistance against movement of the plunger rod may be performed simultaneously with moving 6024 the plunger rod to the first plunger rod position, as illustrated. Detecting 6026 resistance against movement of the plunger rod may be indicative of cartridge parameters of the cartridge received, such as whether the cartridge is new or used or flawed.

Moving 6004 the plunger rod to the mix plunger rod position may follow reading 6020 the cartridge code feature, receiving 6002 the temperature signal, detecting 6022 needle cover removal, moving 6024 the plunger rod to the pre-mix plunger rod position, detecting 6026 resistance against movement of the plunger rod, and determining 6018 orientation of the cartridge.

Moving 6004 the plunger rod to the mix plunger rod position may be based on one or more of the cartridge code feature, the temperature, needle cover removal, resistance against movement of the plunger rod and/or orientation of the cartridge.

Moving 6006 the plunger rod to the second plunger rod position may require that a reconstitution time has elapsed since completion of movement of the plunger rod to the mix plunger rod position. The method 6000" comprises a step of determining 6019 the reconstitution time. Determining 6019 the reconstitution time may be based on one or more of the cartridge code feature, the temperature, needle cover removal, resistance against movement of the plunger rod and/or orientation of the cartridge. Determining 6019 the reconstitution time may comprise determining a first movement parameter, such as an amount of movement of the auto injector, such as shaking the auto injector and/or a number of inversions of the auto injector. The first movement parameter may be determined based on an orientation signal, such as from an orientation sensor, such as an accelerometer. Determining 6019 the reconstitution time may comprise receiving an orientation signal.

Determining 6019 the reconstitution time may be determined based on a combination of the first movement parameter, the temperature and/or the cartridge code feature. Receiving 6002 the temperature signal may be performed additionally or alternatively while determining 6019 the reconstitution time, such as to determine the reconstitution time.

Moving 6006 the plunger rod to the second plunger rod position may be based on one or more of the cartridge code feature, the temperature, needle cover removal, resistance against movement of the plunger rod and/or orientation of the cartridge.

Moving 6010 the plunger rod to the injection plunger rod position may be based on one or more of the cartridge code feature, the temperature, needle cover removal and/or resistance against movement of the plunger rod.

The method 6000 and/or the method 6000' and/or the method 6000" may include a first step of receiving the cartridge.

FIGS. 13*a-d* schematically illustrates an exemplary user interface 1100 of an exemplary auto injector 4, such as an auto injector 4 as illustrated in FIG. 1.

The user interface 1100 comprises a first output member 1110 as illustrated, e.g. a plurality of LEDs. The first output member 1110 may provide for a user output to a user. The first output member 1110 may be used to indicate a step in the procedure to the user and/or to indicate an error message. The first output member 1110 comprises a first LED 1116, a second LED 1118, and a third LED 1120.

The user interface 1100 may comprise a second output member (not shown), e.g. a speaker.

The user interface 1100 comprises a contact member 1102, e.g. at a forward end of the auto injector 4. The contact member 1102 may be configured to be pressed against an injection site. The contact member 1102 may serve as a third output member of the user interface 1100, e.g. the contact member 1102 may be configured to light up, such as flash.

The user interface 1100 comprises a first input member 1108, e.g. a button. The first input member 1108 may provide for a user input from a user. For example, the first input member 1108 may be used for receiving a push from a user to proceed to a next step. The first input member 1108 may serve as a fourth output member of the user interface 1100, e.g. the first input member 1108 may be configured to light up, such as flash.

FIG. 13*a* schematically illustrates a situation of the user interface 1100 wherein none of the output members are active, e.g. the auto injector 4 may be turned off.

FIG. 13*b* schematically illustrates a situation of the user interface 1100 wherein the first input member 1108 and the contact member 1102 light up, such as flashes. The first input member 1108 and the contact member 1102 may flash synchronously and/or asynchronously. The situation shown may be a situation indicating that the user should press the first input member 1108 and/or insert a cartridge though the contact member 1102. The situation shown may be a situation following that the auto injector is turned on.

FIG. 13*c* schematically illustrates a situation of the user interface 1100 wherein the first input member 1108 and the second LED 1118 light up, such as flashes. The situation shown may be a situation indicating that the user should press the first input member 1108 to proceed to a next step. The situation shown may be a situation following mixing of medicament components and/or before performing an airshot.

FIG. 13d schematically illustrates a situation of the user interface 1100 wherein the first input member 1108 and the contact member 1102 and the third LED 1120 light up, such as flashes. The first input member 1108 and the contact member 1102 and the third LED 1120 may flash synchronously and/or asynchronously. The situation shown may be a situation indicating that the user should press the contact member 1102 against an intended injection site to inject the medicament. The situation shown may be a situation before injecting the medicament.

FIG. 14a-c schematically illustrate an exemplary movement of an exemplary auto injector 4, such as a movement of the first movement parameter.

FIG. 14a shows the auto injector 4 in a first position, wherein a first end 4a of the auto injector 4 points substantially upwards. A second end 4b of the auto injector 4 points substantially downwards.

FIG. 14b shows the auto injector 4 having been moved to a second position, wherein the first end 4a of the auto injector 4 points substantially downwards. The second end 4b of the auto injector 4 points substantially upwards.

FIG. 14c shows the auto injector 4 having been moved to a third position, such as back to the first position, wherein the first end 4a of the auto injector 4 points substantially upwards. The second end 4b of the auto injector 4 points substantially downwards.

The first movement parameter may be indicative of number of inversions of the auto injector 4, such as number of times the auto injector 4 has been moved from the first position to the second position and optionally to the third position, such as back to the first position. The processing unit (not shown in FIG. 14) may be configured to detect and/or count number of inversions.

Although, in the example shown, the first end 4a of the auto injector 4 in the first and third positions points directly upwards, it may be enough that the first end 4a of the auto injector 4 points within e.g. 45 degrees of upwards.

Similarly, although in the example shown, the first end 4a of the auto injector 4 in the second position points directly downwards, it may be enough that the first end 4a of the auto injector 4 points within e.g. 45 degrees of downwards.

Figure 14:
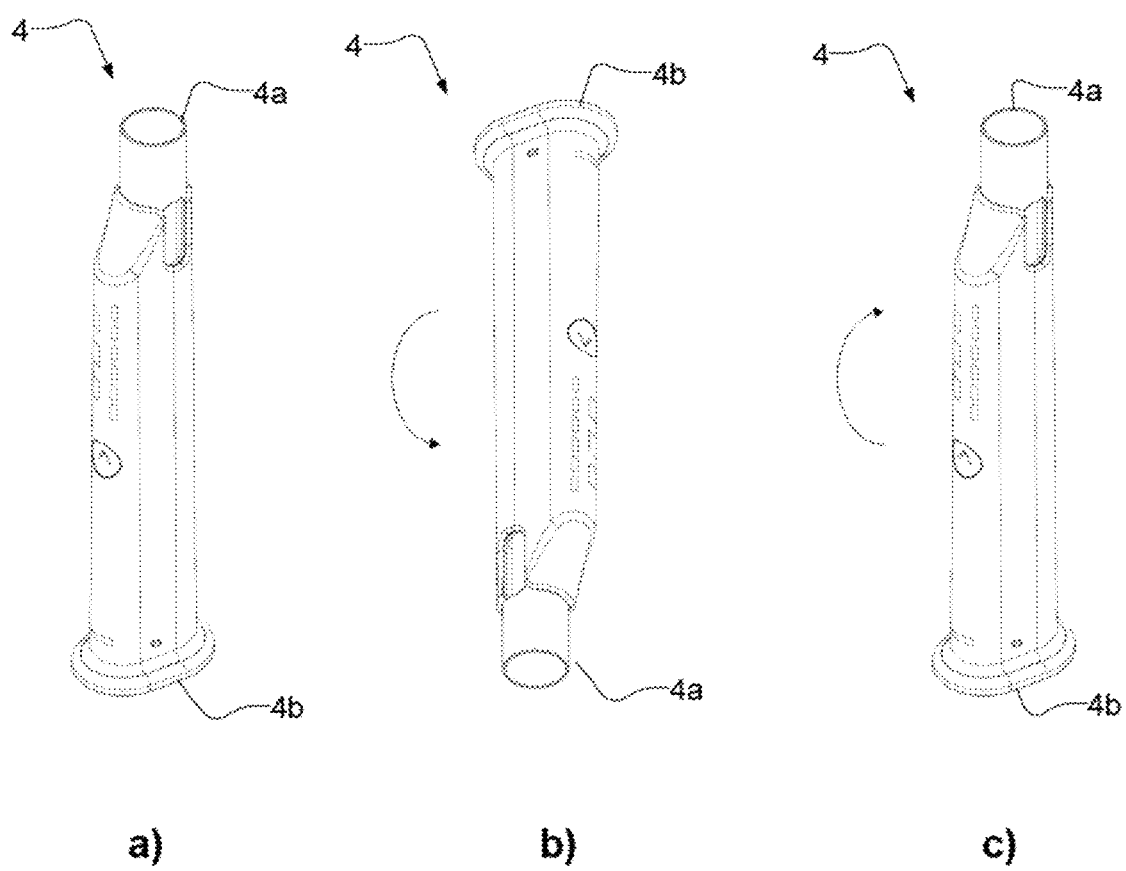
FIG. 14 *a-c* schematically illustrate an exemplary movement of an exemplary auto injector.

The reconstitution time may be dependent on inversions as described in relation to FIG. 14. For example, reconstitution may require a certain number of inversions being performed, such as 5, with a frequency within a predefined range of frequencies, such as between 0.3 and 1.2 Hz. For example the reconstitution time may be the time used to perform the number of inversions. The number of inversions necessary and/or the range of frequencies may be determined based on the temperature, e.g. for higher temperatures less inversions may be needed, and for lower temperatures more inversions may be needed. Alternatively or additionally, the number of inversions necessary and/or the range of frequencies may be determined based on the cartridge code feature, e.g. the cartridge code feature may be indicative of the number of inversions and/or frequency range for the inversions.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. An auto injector for administering a medicament, the auto injector comprising:
   a housing;
   a cartridge receiver configured to receive a cartridge comprising a first stopper and a cartridge compartment containing the medicament, the cartridge compartment having a first cartridge subcompartment containing a first medicament component of the medicament and a second cartridge subcompartment containing a second medicament component of the medicament;
   a drive module coupled to move a plunger rod between a retracted plunger rod position and an extended plunger rod position, the plunger rod being configured to move the first stopper;
   a temperature sensor configured to provide a temperature signal indicative of the temperature of one or more of the auto injector, the cartridge, and the medicament in the cartridge;
   an orientation sensor configured to provide an orientation signal indicative of the orientation of the cartridge;
   a processing unit coupled to the temperature sensor, the drive module and the orientation sensor;
   wherein the processing unit is configured to:
      receive the temperature signal;
      control the drive module to move the plunger rod from a first plunger rod position to a mix plunger rod position with a mix plunger rod speed, wherein the mix plunger rod position is selected to position the first stopper in a position wherein the first medicament component is mixed with the second medicament component;
      determine a first movement parameter based on the orientation signal, wherein the first movement parameter is indicative of a number of inversions of the auto injector; and
      control the drive module to move the plunger rod from the mix plunger rod position to a second plunger rod position after a reconstitution time has elapsed since completion of movement of the plunger rod to the mix plunger rod position, wherein the reconstitution time is based on a predefined number of inversions, which have been completed; the predefined number of inversions being based on the temperature signal.

2. The auto injector according to claim 1, wherein predefined number of inversions are between 1 and 10.

3. The auto injector according to claim 1, wherein the predefined number of inversions are between 3 and 7.

4. The auto injector according to claim 1, wherein the predefined number of inversions is 5.

5. The auto injector according to claim 1, wherein the reconstitution time is based on the temperature signal.

6. The auto injector according to claim 1, wherein the first plunger rod position or the mix plunger rod position is based on the temperature signal.

7. The auto injector according to claim 1, wherein the mix plunger rod speed is based on the temperature signal.

8. The auto injector according to claim 1, wherein the cartridge receiver is configured to receive a cartridge assembly comprising the cartridge and a cartridge code feature, and the auto injector comprising a code sensor configured to read the cartridge code feature, and wherein the processing unit is coupled to the code sensor and further configured to receive from the code sensor a code signal indicative of the cartridge code feature, and wherein the movement from the first plunger rod position to the mix plunger rod position is based on the code signal.

9. The auto injector according to claim 8, wherein the reconstitution time is based on the code signal.

10. The auto injector according to claim 8, wherein the first plunger rod position or the mix plunger rod position is based on the code signal.

11. The auto injector according to claim 8, wherein the mix plunger rod speed is based on the code signal.

12. The auto injector according to claim 1, wherein the processing unit is coupled to the orientation sensor and further configured to receive the orientation signal, and wherein the movement from the first plunger rod position to the mix plunger rod position is based on the orientation signal.

13. The auto injector according to claim 12, wherein the mix plunger rod speed is based on the orientation signal.

14. The auto injector according to claim 1, wherein the processing unit is further configured to determine a first movement parameter based on cumulative movement of the auto injector.

15. The auto injector according to claim 14, wherein the reconstitution time is based on the first movement parameter.

16. The auto injector according to claim 14, wherein the mix plunger rod speed is based on the first movement parameter.

17. The auto injector according to claim 14, wherein the first movement parameter is indicative of number of inversions of the auto injector.

18. The auto injector according to claim 14, wherein the first movement parameter is indicative of a frequency of movement of the auto injector.

19. The auto injector according to claim 1, wherein the temperature sensor comprises an infrared sensor.

20. The auto injector according to claim 1, further comprising a temperature control unit configured to alter the temperature of the cartridge when received in the cartridge receiver.

21. The auto injector according to claim 20, wherein the temperature control unit is configured to raise the temperature of the cartridge.

22. The auto injector according to claim 21, wherein the temperature control unit comprises a resistive heating element.

23. The auto injector according to claim 21, wherein the temperature control unit comprises a dielectric heating element.

24. The auto injector according to claim 20, wherein the temperature control unit is configured to lower the temperature of the cartridge.

25. The auto injector according to claim 20, wherein the temperature control unit comprises a thermoelectric element, such as a Peltier element.

26. The auto injector according to claim 20, wherein the temperature control unit comprises a contact element configured to be in contact with the cartridge when received in the cartridge receiver.

27. The auto injector according to claim 20, wherein the temperature control unit comprises a coil element configured to surround an entire perimeter of the cartridge when received in the cartridge receiver.

28. The auto injector according to claim 1, wherein the first plunger rod position is a pre-mix plunger rod position, and the pre-mix plunger rod position is selected to position the first stopper in a position wherein fluid communication between the first cartridge subcompartment and the second cartridge subcompartment is not yet established.

29. The auto injector according to claim 1, wherein the second plunger rod position is a prime plunger rod position, and the prime plunger rod position is selected to position the first stopper in a position wherein air in the cartridge compartment is reduced to an amount appropriate for injection.

30. The auto injector according to claim 1, wherein the processing unit is configured to control the drive module to move the plunger rod to an injection plunger rod position, and the injection plunger rod position is selected to position the first stopper in a position wherein medicament in the cartridge compartment is minimized.

31. The auto injector according to claim 30, wherein the processing unit is further configured to:
receive a trigger event; and
control the drive module to move the plunger rod to the injection plunger rod position following reception of the trigger event.

32. A method for operating an auto injector comprising a cartridge receiver configured to receive a cartridge comprising a first stopper and a cartridge compartment containing the medicament, the cartridge compartment having a first cartridge subcompartment containing a first medicament component of the medicament and a second cartridge subcompartment containing a second medicament component of the medicament, a plunger rod configured to move the first stopper, and a temperature sensor, the method comprising:
receiving the temperature signal from the temperature sensor indicative of the temperature of the medicament when the cartridge is received in the cartridge receiver;
moving the plunger rod from a first plunger rod position to a mix plunger rod position with a mix plunger rod speed, wherein the mix plunger rod position is selected to position the first stopper in a position wherein the first medicament component is mixed with the second medicament component;
determining a first movement parameter based on the orientation signal, wherein the first movement parameter is indicative of a number of inversions of the auto injector;
moving the plunger rod from the mix plunger rod position to a second plunger rod position after a reconstitution time has elapsed since completion of movement of the plunger rod to the mix plunger rod position, wherein the reconstitution time is based on a predefined number of inversions have been completed; the predefined number of inversions are based on the temperature signal indicative of the temperature of the medicament.

33. The method according to claim 32, wherein the second plunger rod position is a prime plunger rod position, the prime plunger rod position being selected to position the first stopper in a position wherein air in the cartridge compartment is reduced to an amount appropriate for injection.

* * * * *

UNITED STATES PATENT AND TRADEMARK OFFICE
CERTIFICATE OF CORRECTION

PATENT NO. : 12,296,148 B2
APPLICATION NO. : 17/741314
DATED : May 13, 2025
INVENTOR(S) : Per Mølgaard Pedersen It is certified that error appears in the above-identified patent and that said Letters Patent is hereby corrected as shown below:

In the Specification

In Column 11, Line 34, delete "of upwards" and insert --of upwards.--.

Figure 4:
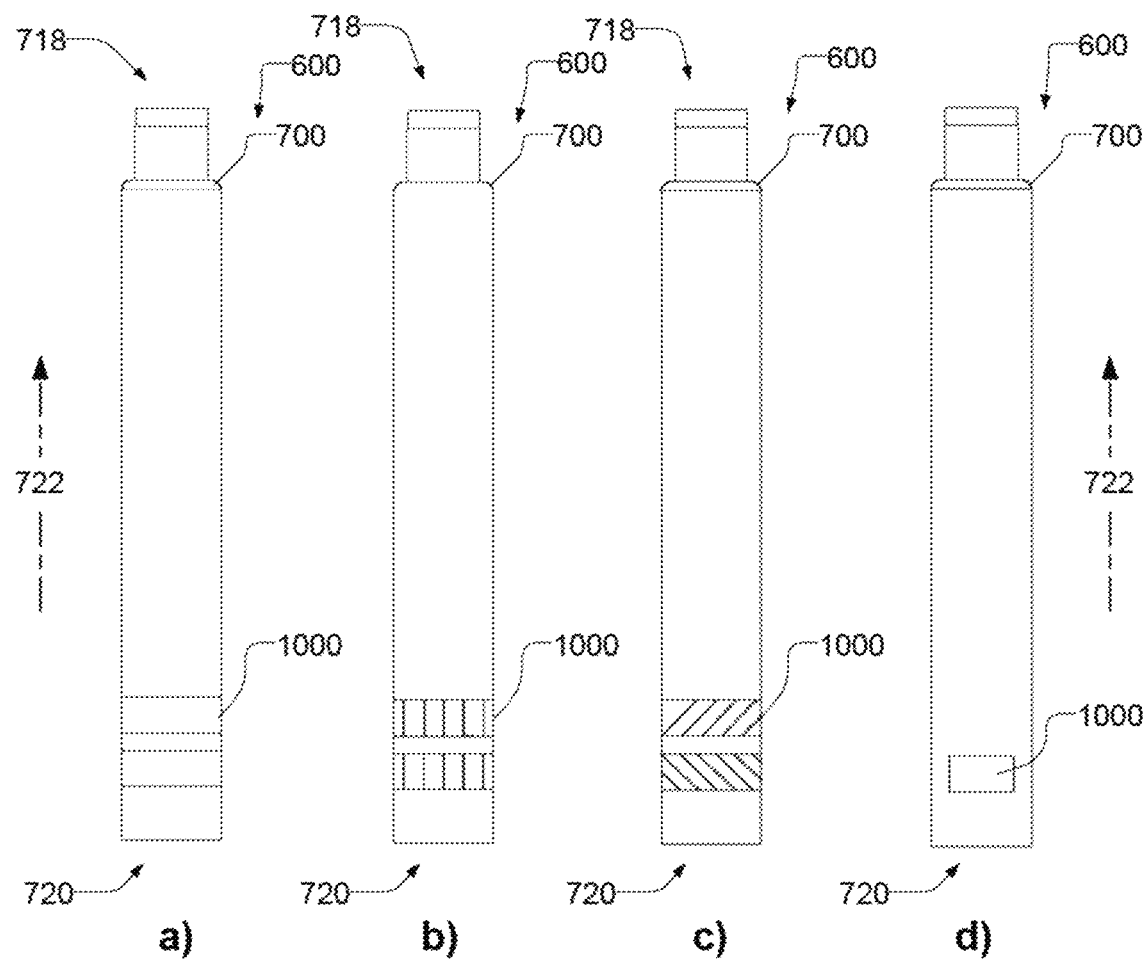
FIG. 4 *a-d* schematically illustrate an exemplary cartridge assembly with exemplary cartridge code features.

In Column 19, Line 58, delete "FIG. 4 a-d schematically" and insert --FIGS. 4a-d schematically--.

In Column 19, Line 62, delete "FIG. 6 a-d schematically" and insert --FIGS. 6a-d schematically--.

Figure 8:
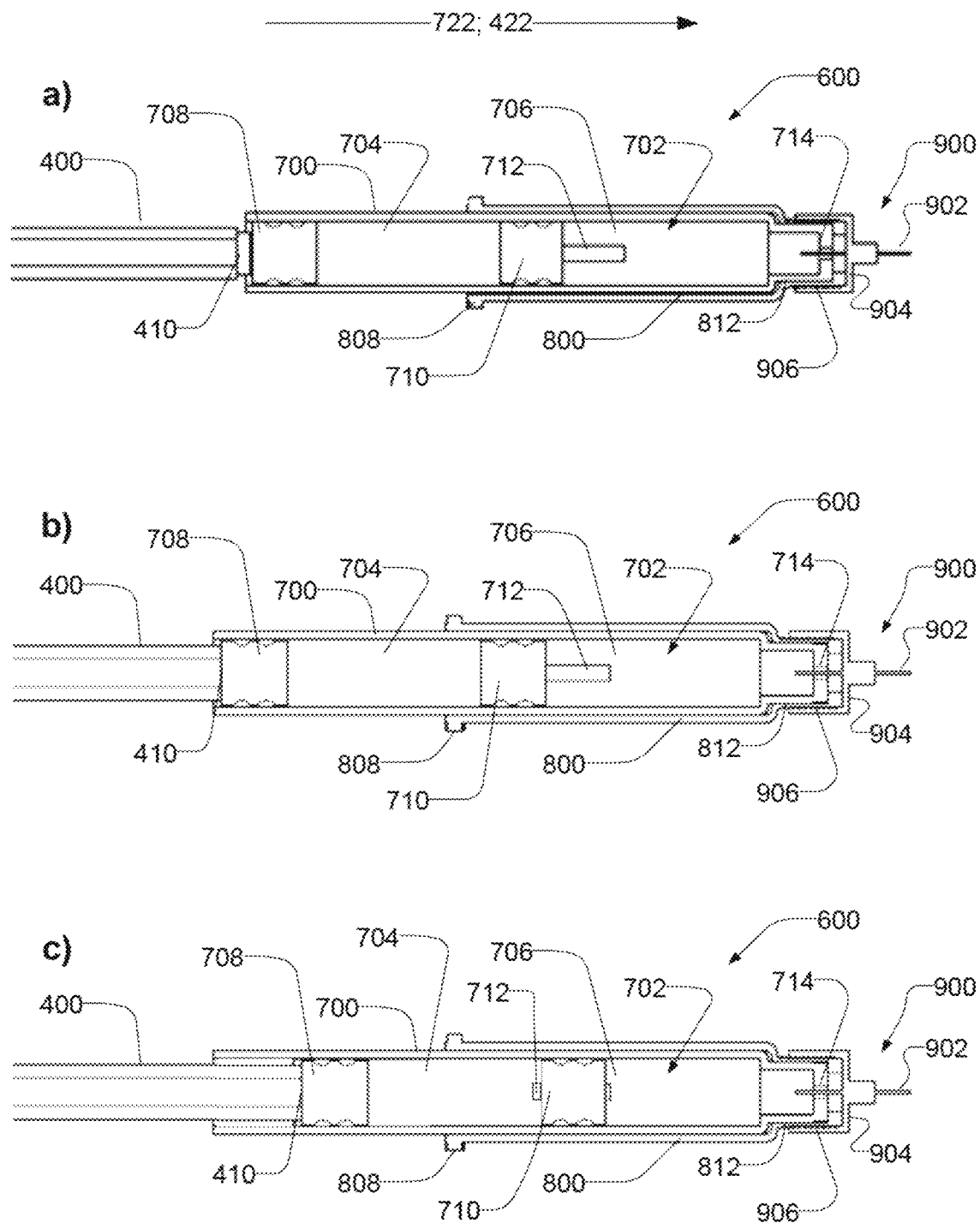
FIG. 8 *a-f* schematically illustrate an exemplary cartridge assembly and a plunger rod in exemplary positions.
Figure 8:
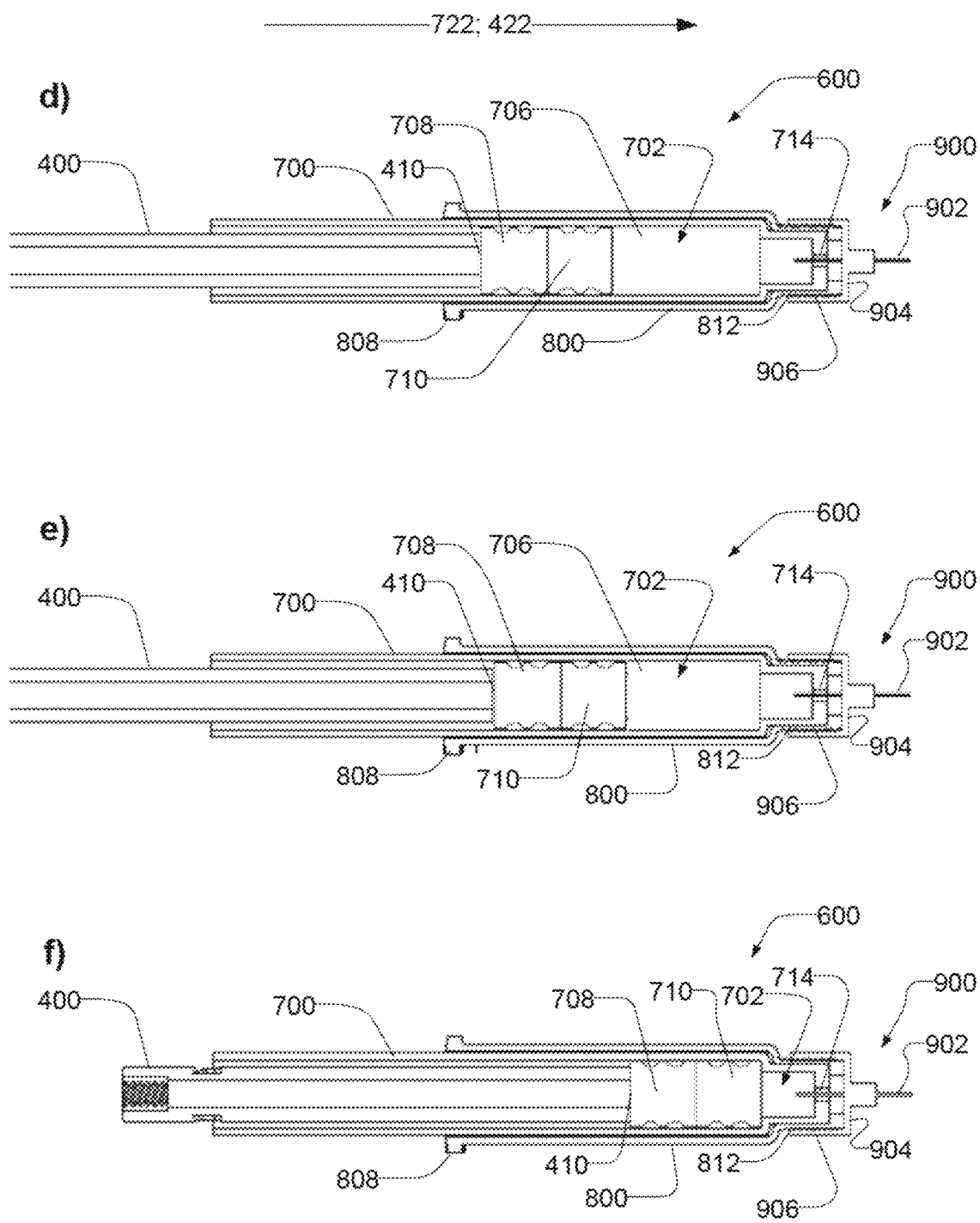

In Column 19, Line 66, delete "FIG. 8 a-f schematically" and insert --FIGS. 8a-f schematically--.

Figure 13:
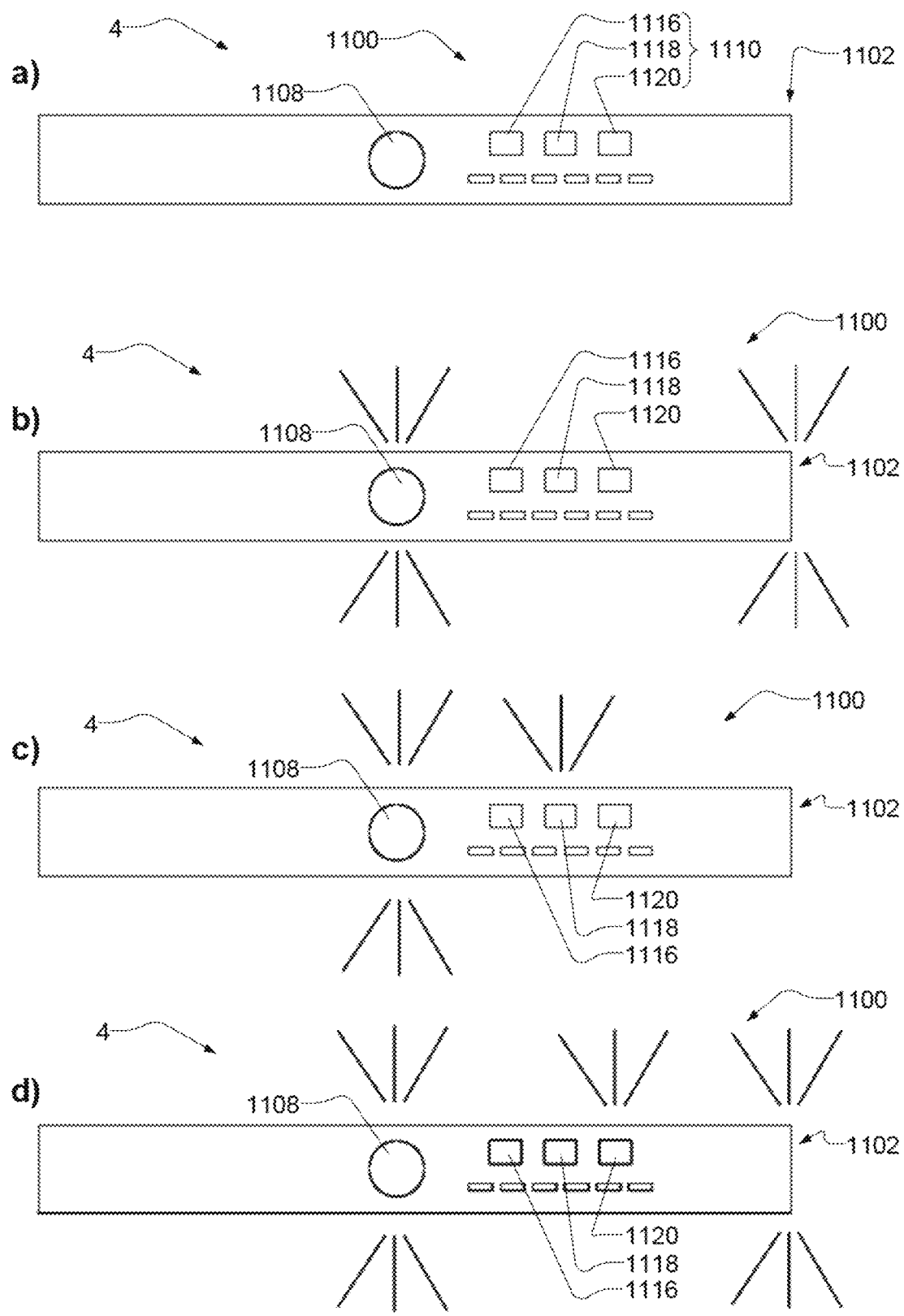
FIG. 13 *a-d* schematically illustrate an exemplary user interface.

In Column 20, Line 6, delete "FIG. 13 a-d schematically" and insert --FIGS. 13a-d schematically--.

In Column 20, Line 8, delete "FIG. 14 a-c schematically" and insert --FIGS. 14a-c schematically--.

In Column 32, Line 9, delete "rod position" and insert --rod position.--.

In Column 33, Line 12 (Approx.), delete "temperature signal" and insert --temperature signal.--.

In Column 35, Line 12 (Approx.), delete "FIG. 14a-c schematically" and insert --FIGS. 14a-c schematically--.

Signed and Sealed this
Twenty-second Day of July, 2025

Coke Morgan Stewart
*Acting Director of the United States Patent and Trademark Office*